(12) United States Patent
Chatterjee

(10) Patent No.: US 9,134,315 B2
(45) Date of Patent: Sep. 15, 2015

(54) USE OF THE LACTOSYLCERAMIDE SYNTHASE ISOFORM B1,4GALT-V AS A BIOMARKER FOR CANCER

(75) Inventor: Subroto Chatterjee, Columbia, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 13/578,657

(22) PCT Filed: Feb. 12, 2010

(86) PCT No.: PCT/US2010/024047
§ 371 (c)(1),
(2), (4) Date: Nov. 2, 2012

(87) PCT Pub. No.: WO2011/099980
PCT Pub. Date: Aug. 18, 2011

(65) Prior Publication Data
US 2013/0041015 A1 Feb. 14, 2013

(51) Int. Cl.
*C12Q 1/68* (2006.01)
*G01N 33/574* (2006.01)
*C12Q 1/48* (2006.01)

(52) U.S. Cl.
CPC ............ *G01N 33/57484* (2013.01); *C12Q 1/48* (2013.01); *G01N 33/57419* (2013.01); *G01N 33/57438* (2013.01); *G01N 2800/56* (2013.01)

(58) Field of Classification Search
None
See application file for complete search history.

(56) References Cited

U.S. PATENT DOCUMENTS

| | | | |
|---|---|---|---|
| 5,041,441 A | 8/1991 | Radin et al. | |
| 5,707,649 A | 1/1998 | Inokuchi et al. | |
| 5,972,928 A | 10/1999 | Chatterjee | |
| 6,228,889 B1 | 5/2001 | Chatterjee | |
| 6,511,979 B1 | 1/2003 | Chatterjee | |
| 6,569,889 B2 | 5/2003 | Shayman et al. | |
| 2001/0041735 A1 | 11/2001 | Shayman et al. | |
| 2002/0198240 A1 | 12/2002 | Shayman et al. | |
| 2003/0073690 A1 | 4/2003 | Tulshian et al. | |

OTHER PUBLICATIONS

Kolmakova, A., et al., "VEGF recruits lactosylceramide to induce endothelial cell adhesion molecule expression and angiogenesis in vitro and in vivo", Glycoconj. J., Jul. 2009, vol. 26, No. 5, pp. 547-558.

Jiang, J., et al., "Down-regulation of beta1,4-galactosyltransferase V is a critical part of etoposide-induced apoptotic process and could be mediated by decreasing Sp1 levels in human glioma cells", Glycobiology, Nov. 2006, vol. 16, No. 11, pp. 1045-1051.

Wei, Y., et al., "Down-regulation of beta1,4GalT V at protein level contributes to arsenic trioxide-induced glioma cell apoptosis", Cancer Letters, Aug. 2008, vol. 267, No. 1, pp. 96-105.

*Primary Examiner* — Kimberly Chong
(74) *Attorney, Agent, or Firm* — Johns Hopkins Technology Transfer

(57) ABSTRACT

In one aspect, B1,4GalT-V, an isoform of the enzyme lactosylceramide synthase, is provided as a biomarker for cancer. Also provided are methods and compositions directed at cancers characterized by the overexpression or upregulation of the lactosylceramide synthase isoform B1,4GalT-V.

3 Claims, 9 Drawing Sheets

USE OF THE LACTOSYLCERAMIDE SYNTHASE ISOFORM B1,4GALT-V AS A BIOMARKER FOR CANCER

CROSS-REFERENCE TO RELATED APPLICATIONS

This application is a 35 U.S.C. §371 U.S. national entry of International Application PCT/US2010/024047 having an international filing date of Feb. 12, 2010, the content of which is herein incorporated by reference in its entirety.

FIELD OF THE INVENTION

The field of the invention relates to cancer. More specifically, the present invention relates to the use of B1,4GalT-V, an isoform of the enzyme lactosylceramide synthase, as a biomarker for cancer.

BACKGROUND OF THE INVENTION

In spite of numerous advances in medical research, cancer remains a major cause of death worldwide. There is a tremendous need for rapid and simple methods for the early diagnosis of cancer to facilitate appropriate remedial action by surgical resection, radiotherapy, chemotherapy, or other known treatment methods. The availability of good diagnostic methods for cancer is also important to assess patient responses to treatment, or to assess recurrence due to re-growth at the original site or metastases.

The characterization of cancer biomarkers including, for example, oncogene products, growth factors and growth factor receptors, angiogenic factors, proteases, adhesion factors and tumor suppressor gene products, etc., can provide important information concerning the risk, presence, status or future behavior of cancer in a human or non-human mammalian subject. Determining the presence or level of expression or activity of one or more cancer biomarkers can assist the differential diagnosis of patients with uncertain clinical abnormalities, for example, by distinguishing malignant from benign abnormalities. In patients presenting with established malignancy, cancer biomarkers can be useful to predict the risk of future relapse, or the likelihood of response in a particular patient to a selected therapeutic course. Even more specific information can be obtained by analyzing highly specific cancer biomarkers, or combinations of biomarkers, which may predict responsiveness of a patient to specific drugs or treatment options. Furthermore, cancer biomarkers can be used as targets for developing new and useful therapeutics.

Accordingly, a great need exists for specific and sensitive biomarkers that can predict the biological behavior of cancer cells, as well as improved methods to specifically detect, characterize, and monitor the specific types and progression of cancer.

SUMMARY OF THE INVENTION

The present invention relates to the treatment of cancer. More specifically, the present invention provides methods and compositions directed at cancers characterized by the overexpression or upregulation of the lactosylceramide synthase iso form B1,4GalT-V.

In one aspect, B1,4GalT-V may be used a biomarker for cancer. In one embodiment, a method for qualifying cancer status in a subject may comprise measuring the B1,4GalT-V biomarker in a biological sample from the subject, and correlating the measurement with cancer status. In another embodiment, at least one other biomarker in the biological sample may be measured and correlated with B1,4GalT-V with cancer status. Any type of cancer in which B1,4GalT-V is upregulated may be tested including, but not limited to, colorectal, renal, and pancreatic. In several embodiments, the biomarkers, including B1,4GalT-V, may be measured by immunoassay, specifically, an ELISA. The samples to be tested may be blood, serum, or stool.

In another aspect, the present invention provides methods and compositions directed at treating or preventing a B1,4GalT-V related cancer. The B1,4GalT-V therapeutic agents may comprise molecules that inhibit the expression of B1,4GalT-V. For example, therapeutic agents may direct RNA interference that inhibits B1,4GalT-V expression. In certain embodiments, the therapeutic agents may comprise small-interfering RNA, antisense oligonucleotides, or ribozymes.

In one embodiment, the present invention provides a method for treating a B1,4GalT-V related cancer in a subject comprising the step of administering to the subject an RNA interference (RNAi) inducing entity. The method may further comprise administering an additional therapeutic agent to said subject.

In a specific embodiment, the RNAi inducing entity may comprise an RNAi construct that attenuates the expression of the B1,4GalT-V gene. Moreover, the RNAi construct may be an expression vector having a coding sequence that is transcribed to produce one or more transcriptional products that produce siRNA in the cells of the subject. In an alternative embodiment, the RNAi inducing entity may comprise a small-interfering RNA (siRNA). For example, the siRNA may be 15-40 base pairs long.

The present invention further provides a method for treating a B1,4GalT-V related cancer in a subject comprising administering to the subject a compound comprising a double stranded RNA comprising at least a portion of the B1,4GalT-V nucleic acid sequence, wherein the administering is sufficient to treat the B1,4GalT-V related cancer in the subject. Alternatively, a method for treating a B1,4GalT-V related cancer in a subject may comprise administering to the subject a single-stranded small interfering RNA molecule (ss-siRNA) wherein the sequence of the ss-siRNA is sufficiently complementary to a target B1,4GalT-V mRNA sequence to direct target-specific RNA interference.

In other embodiments, the B1,4GalT-V therapeutic agents may inhibit the function or action of B1,4GalT-V. More specifically, the B1,4GalT-V therapeutic agent may comprise an antibody. As described more fully below, the antibodies may comprise synthetic antibodies, polyclonal antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv) (including bi-specific scFvs), single chain antibodies Fab fragments, F(ab') fragments, disulfide-linked Fvs (sdFv), and anti-idiotypic (anti-Id) antibodies, and epitope-binding fragments of any of the above.

The present invention also provides methods and composition utilizing small molecule inhibitors of B1,4GalT-V. In a specific embodiment, a method for treating a B1,4GalT-V related cancer in a subject comprises the step of administering to the subject a therapeutically effective amount of D-threo-1-phenyl-2-decanoyl-3-morpholino-1-propanol (D-PDMP). In other embodiments, derivatives of D-PDMP may be used.

The detailed description below provides further embodiments and alternatives useful in the methods of compositions of the present invention.

DETAILED DESCRIPTION OF THE INVENTION

Figure 1:
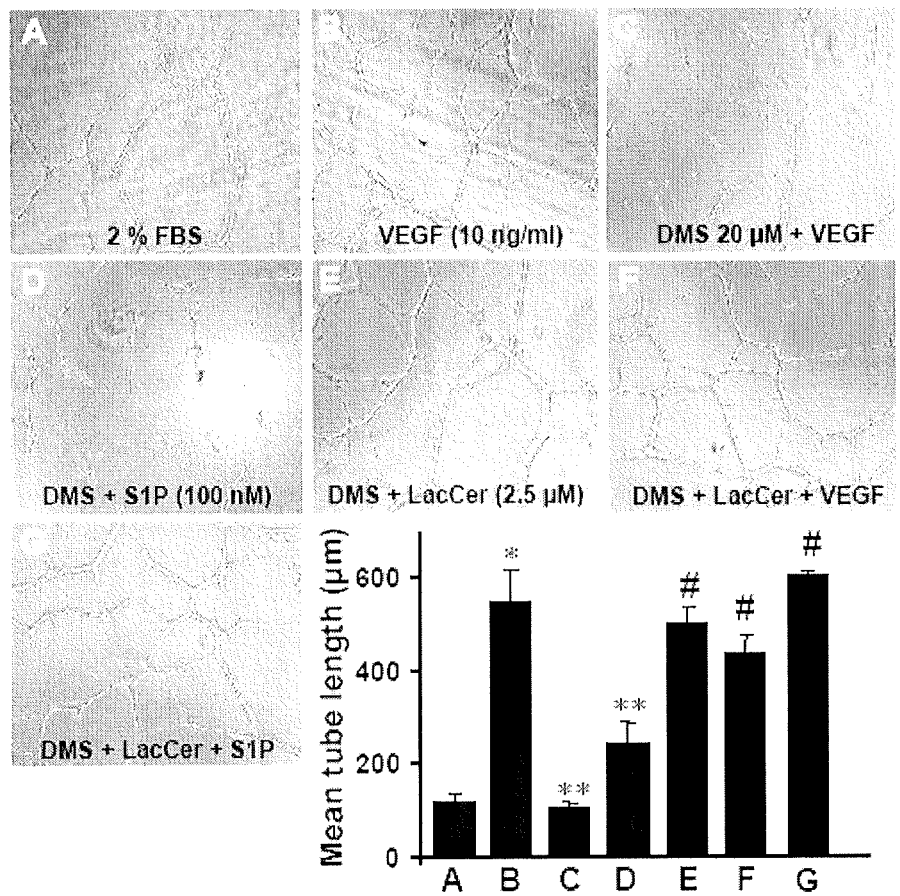
FIG. 1 demonstrates that VEGF-induced tube formation was inhibited by DMS and this was bypassed by LacCer but not S1P. HUVECs were pre-treated with the inhibitors with the concentrations indicated and then in vitro tube formation assays were performed as described below. *$P<0.001$ vs. 2% FBS; **$P<0.001$ vs. VEGF; # $P<0.001$ vs. DMS or DMS+S1P (n=9).

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

As used herein, and unless otherwise indicated, the term "antisense oligonucleotide" refers to an oligonucleotide having a sequence complementary to a target DNA or RNA sequence.

As used herein, the term "antisense strand" of an siRNA or RNAi agent e.g., an antisense strand of an siRNA duplex or siRNA sequence, refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific RNA interference (RNAi), e.g., complementarity sufficient to trigger the destruction of the desired target mRNA by the RNAi machinery or process. The term "sense strand" or "second strand" of a siRNA or RNAi agent e.g., an antisense strand of an siRNA duplex or siRNA sequence, refers to a strand that is complementary to the antisense strand or first strand. Antisense and sense strands can also be referred to as first or second strands, the first or second strand having complementarity to the target sequence and the respective second or first strand having complementarity to said first or second strand.

The terms "B1,4GalT-V related cancer, "B1,4GalT-V related disorder," "cancer associated with the overexpression of B1,4GalT-V" are used interchangeably herein, and include any cancer, pre-cancer, or disorder that involves a change in the expression of the B1,4GalT-V, either at the protein or RNA level.

As used herein, and unless otherwise indicated, the term "B1,4GalT-V siRNA" denotes a small interfering RNA that has a sequence complementary to a sequence within the B1,4GalT-V gene.

As used herein, "comparing" in relation to "the proportion, level, or cellular localization, to a standard proportion, level, or cellular localization" refers to making an assessment of the how the proportion, level, or cellular localization of a B1,4GalT-V-related transcript or protein in a sample relates to the proportion, level, or cellular localization of a B1,4GalT-V-related transcript or protein of the standard. For example, assessing whether the proportion, level, or cellular localization of the B1,4GalT-V-related transcript or protein of the sample is the same as, more or less than, or different from the proportion, level, or cellular localization B1,4GalT-V-related transcript or protein of the standard or control.

As used herein, and unless otherwise indicated, the term "complementary," when used to describe a sequence in relation to a target sequence, means that the sequence is able to bind to the target sequence in a cellular environment in a manner sufficient to disrupt the function (e.g., replication, splicing, transcription or translation) of the gene comprising the target sequence. The binding may result from interactions such as, but not limited to, nucleotide base parings (e.g., A-T/G-C). In particular embodiments of the invention, a sequence is complementary when it hybridizes to its target sequence under high stringency, e.g., conditions for hybridization and washing under which nucleotide sequences, which are at least 60 percent (preferably greater than about 70, 80, or 90 percent) identical to each other, typically remain hybridized to each other. Such stringent conditions are known to those skilled in the art, and can be found, for example, in Current Protocols in Molecular Biology, John Wiley & Sons, N.Y. (1989), 6.3.1-6.3.6, which is incorporated herein by reference. Another example of stringent hybridization conditions is hybridization of the nucleotide sequences in 6× sodium chloride/sodium citrate (SSC) at about 45° C., followed by 0.2×SSC, 0.1% SDS at 50-65° C. Particularly preferred stringency conditions are hybridization in 6× sodium chloride/sodium citrate (SSC) at about 45° C., followed by one or more washes in 0.2.×SSC, 0.1% SDS at 50° C. Depending on the conditions under which binding sufficient to disrupt the functions of a gene occurs, a sequence complementary to a target sequence within the gene need not be 100 percent identical to the target sequence. For example, a sequence can be complementary to its target sequence when at least about 70, 80, 90, or 95 percent of its nucleotides bind via matched base pairings with nucleotides of the target sequence.

As used herein, "correlating" in reference to a parameter, e.g., a modulated proportion, level, or cellular localization in the cell from the subject, may be an indication that the cancer is likely a B1,4GalT-V related cancer. "Correlating" or "normalization" as used according to the present invention may be by any method of relating levels of expression or localization of markers to a standard valuable for the: assessment of the diagnosis, prediction of a cancer or cancer progression, assessment of efficacy of clinical treatment, identification of a tumor that may respond to a B1,4GalT-V treatment, selection of a subject for a particular treatment, monitoring of the progress of treatment with a B1,4GalT-V directed therapy, and in the context of a screening assay, for the identification of a B1,4GalT-V related cancer therapeutic.

When used to describe the sequences of siRNAs, the term "corresponding to," as used herein, means that a siRNA has a sequence that is identical or complementary to the portion of target mRNA that is transcribed from the denoted DNA sequence.

As used herein, and unless otherwise indicated, the term "inhibiting the synthesis or expression" of a gene means impeding, slowing or preventing one or more steps by which the end-product protein encoded by said gene is synthesized. Typically, the inhibition involves blocking of one or more steps in the gene's replication, transcription, splicing or translation through a mechanism that comprises recognition of a target site located within the gene or transcript sequence based on sequence complementation. In a specific embodiment, inhibition of B1,4GalT-V reduces the amount of B1,4GalT-V in the cancer cell by greater than about 20%, 40%, 60%, 80%, 85%, 90%, 95%, or 100%. The amount of B1,4GalT-V can be determined by well-known methods including, but are not limited to, densitometer, fluorometer, radiography, luminometer, antibody-based methods and activity measurements.

As used herein, the term "isolated RNA" (e.g., "isolated ssRNA", "isolated siRNA" or "isolated ss-siRNA") refers to RNA molecules which are substantially free of other cellular material, or culture medium when produced by recombinant techniques, or substantially free of chemical precursors or other chemicals when chemically synthesized.

The term "measuring" means methods which include detecting the presence or absence of a biomarker(s) in a sample, quantifying the amount of biomarker(s) in the sample, and/or qualifying the type of biomarker(s). Measuring can be accomplished by methods known in the art and those further described herein including, but not limited to, immunoassay.

As used herein, the term "molecule" when used without other qualification, e.g., nucleic acid molecule, refers to both compounds of biological origin or character (e.g., proteins, DNA, RNA, antibodies, etc.) and compounds which are synthetic organic compounds (e.g., aspirin, ibuprofen, ampicillin, etc.).

The term "sample," as used herein, refers to a biological sample obtained for the purpose of evaluation in vitro. In the methods of the present invention, the sample or patient sample may comprise any body fluid including, but not limited to, blood, serum, plasma, urine, saliva, and synovial fluid. A sample may also comprise any cells, tissue samples or cell components (such as cellular membranes or cellular components) obtained from a patient including a tissue biopsy. In a further embodiment, a sample may refer to a stool sample.

An RNAi agent having a strand which is "sequence sufficiently complementary to a target mRNA sequence to direct target-specific RNA interference (RNAi)" means that the strand has a sequence sufficient to trigger the destruction of the target mRNA by the RNAi machinery or process.

The terms "subject" or "patient" are used interchangeably herein, and is meant a mammalian subject to be treated, with human subjects being preferred. In some cases, the terms may refer to treatment in experimental animals, in veterinary application, and in the development of animal models for disease, including, but not limited to, rodents including mice, rats, and hamsters; and primates.

Various methodologies of the instant invention include step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, for example, as described herein. In one embodiment, a transcription rate, mRNA level, translation rate, protein level, biological activity, cellular characteristic or property, genotype, phenotype, etc. can be determined prior to introducing a siRNA of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

A "target gene" is a gene whose expression is to be selectively inhibited or "silenced." In certain embodiments, this silencing is achieved by cleaving the mRNA of the target gene by an siRNA that is created from an engineered RNA precursor by a cell's RNAi system. One portion or segment of a duplex stem of the RNA precursor is an anti-sense strand that is complementary, e.g., fully complementary, to a section of about 18 to about 40 or more nucleotides of the mRNA of the target gene.

The terms "tumor," "solid tumor," "primary tumor," and "secondary tumor" refer to carcinomas, sarcomas, adenomas, and cancers of neuronal origin and, in fact, to any type of cancer which does not originate from the hematopoietic cells and in particular concerns: carcinoma, sarcoma, adenoma, hepatocellular carcinoma, hepatocellular carcinoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, lymphangiosarcoma, synovioma, Ewing's tumor, leiomyosarcoma, rhabdotheliosarcoma, colon carcinoma, pancreatic cancer, breast cancer, ovarian cancer, prostate cancer, squamous cell carcinoma, basal cell carcinoma, adenocarcinoma, renal cell carcinoma, hematoma, bile duct carcinoma, melanoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, retinoblastoma, multiple myeloma, rectal carcinoma, thyroid cancer, head and neck cancer, brain cancer, cancer of the peripheral nervous system, cancer of the central nervous system, neuroblastoma, cancer of the endometrium, as well as metastasis of all the above.

II. Biomarkers

Lactosylceramide (LacCer) is a member of the glycosphingolipid family. It consists of a non-polar component ceramide (sphingosine plus a fatty acid) to which is attached glucose and galactose via a α-1,4 and β-1,4 linkages, respectively. LacCer synthesis is catalyzed by an enzyme LacCer synthase, a Golgi localized enzyme, that transfers galactose residues from UDP-galactose to glucosyl ceramide (GlcCer). Gene mapping studies and recent nomenclature suggest the presence of at least two LacCer synthases in mammalian tissues. For example, B1,4GalT-V is a constitutionally expressed LacCer synthase. Lo et al., 8 Glycobiology 517-26 (1998). In contrast B1,4GalT-VI has a tissue specific expression. Moreover, an alternatively spliced variant of B1,4GalT-VI has also been reported recently. Fan et al., 13 DNA Seq. 1-8 (2003). The exciting feature of this enzyme is that its activity can be transiently increased by diverse physiologically relevant proteins implicated in health and disease. For example, minimally modified LDL, VEGF and TNF-alpha all have been shown to induce the activity of this enzyme to generate LacCer and expression of cell adhesion molecules such as intracellular cell adhesion molecule-1 (ICAM-1), vascular cell adhesion molecular-1 (VCAM-1) and platelet cell adhesion molecule (PECAM-1) and regulate cell proliferation and angiogenesis. See Kolmakova and Chatterjee, 22 Glycoconj. J. 401-07 (2005); Pannu et al., 280 J. Biol. Chem. 13742-51 (2005); Rajesh et al., 97 Circ. Res. 796-804 (2005); Gong et al., 101 Proc. Natl. Acad. Sci. 6490-95 (2004); Pannu et al., 24 J. Neurosci. 5942-54 (2004); Bhunia et al., 273 J. Biol. Chem. 34349-59 (1998); Balagopalakrishna et al., 170 Mol. Cell. Biochem. 85-89 (1997); and Chatterjee et al., 7 Glycobiology 703-10 (1997). Some studies have also suggested the role of sphingosine-1-phosphate in PECAM-1 gene expression (Limayem et al., 105 Blood 3169-77 (2005)) and angiogenesis (Chae et al., 114 J. CLIN. INVEST. 1082-89 (2004)). Interestingly, such phenotypic changes observed in vitro were mitigated by PDMP and inhibitor of GlcCer synthase and LacCer synthase and this was specifically by passed by LacCer. Such studies point to a potential role of LacCer synthase/LacCer in cell proliferation and inflammation.

The study described herein was designed to assess the expression of LacCer synthase in endothelial cells derived from human colon cancer tissue. The study was also designed to determine if VEGF/bFGF-induced angiogenesis in vitro and in vivo requires LacCer synthase/LacCer and to determine the mechanism by which VEGF/LacCer induce angiogenesis. The data show that LacCer can mediate VEGF induced PECAM-1 expression and angiogenesis independent of SIP involvement. It was found that the expression of B1,4GalT-V mRNA transcript was markedly and specifically increased in colon cancer-derived endothelial cells as compared to normal colonic endothelial cells. It was also demonstrated that the LacCer synthase/LacCer pathway is relevant in VEGF/bFGF-induced angiogenesis in vivo.

Accordingly, in one aspect of the present invention, LacCer synthase may be used a biomarker for cancer including, but not limited to, colorectal cancer, renal cancer, pancreatic cancer, and glioblastoma. In one embodiment, the LacCer synthase comprises the B1,4GalT-V isoform. Further embodiments of the present invention include the use of B1,4GalT-V as a biomarker for cancer in combination with one or more biomarkers for cancer in the assessment of cancer in a sample obtained from an individual. For example, the B1,4GalT-V biomarker may be combined with other markers upstream such as vascular endothelial growth factor receptors, as well as mTOR1 and 2 that operate up and down stream of Akt-1.

Furthermore, biomarkers with which the measurement of B1,4GalT-V may be combined include, but are not limited to, Neuron Specific Enolase (NSE), cytokeratin 19 fragment (CYFRA 21-1), nicotinamide N-methyltransferase (NMMT), Carbohydrate Antigen 19-9 (CA 19-9), CA 72-4, and Carcinoembryonic Antigen (CEA). Colorectal cancer biomarkers that may be combined with the B1,4GalT-V biomarker of the present invention include, but are not limited to, proteasome subunit alpha 3 (PSA 3) (U.S. Patent Application Publication No. 2007-0218510), proteasome activator subunit 3 (PSE3) (U.S. Patent Application Publication No. 2006-0199232), 60S acidic ribosomal protein P0 (RLA-0) (U.S. Patent Application Publication No. 2006-0194266), spermidine synthase (SPEE) (U.S. Patent Application Publication No. 2006-0188950), T-plastin (PLST) (U.S. Patent Application Publication No. 2006-0188949), maspin precursor protein (MASP) (U.S. Patent Application Publication No. 2006-0121540), collagen-binding protein 2 (CBP2) (U.S. Patent Application Publication No. 2007-0161062), ribosomal protein S15a (RS15A) (U.S. Patent Application Publication No. 2007-0184498), apoptosis-associated speck-like protein containing a caspase-associated recruitment domain (ASC) (U.S. Patent Application Publication No. 2009-0155820), special AT-rich sequence binding protein 2 (SATB2 protein) (U.S. Patent Application Publication No. 2009-0220975), protein S100A12 (U.S. Patent Application Publication No. 2009-0286328), and/or proteinase 3 (PRN3) bound to leukocyte elastase inhibitor (ILEU) (PRN3/ILEU) (U.S. Patent Application Publication No. 2006-0177880). See Polanski and Anderson, 1 BIOMARKER INSIGHTS 1-48 (2006), which is expressly incorporated herein by reference, for a list of other biomarkers associated with cancer, one or more of which may be used with B1,4GalT-V as described herein.

III. Detection of Biomarkers

A. Detection by Mass Spectrometry

In another aspect, the biomarkers of the present invention may be detected by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these. In a particular method, the mass spectrometer is a laser desorption/ionization mass spectrometer. In a specific embodiment, the mass spectrometric technique comprises surface enhanced laser desorption and ionization or "SELDI," as described, for example, in U.S. Pat. No. 6,225,047 and No. 5,719,060. Briefly, SELDI refers to a method of desorption/ionization gas phase ion spectrometry (e.g. mass spectrometry) in which an analyte (here, one or more of the biomarkers) is captured on the surface of a SELDI mass spectrometry probe. There are several versions of SELDI that may be utilized including, but not limited to, Affinity Capture Mass Spectrometry (also called Surface-Enhanced Affinity Capture (SEAC)), and Surface-Enhanced Neat Desorption (SEND) which involves the use of probes comprising energy absorbing molecules that are chemically bound to the probe surface (SEND probe). Another SELDI method is called Surface-Enhanced Photolabile Attachment and Release (SEPAR), which involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker panel, pursuant to the present invention.

In another mass spectrometry method, the biomarkers can be first captured on a chromatographic resin having chromatographic properties that bind the biomarkers. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

B. Detection by Immunoassay

In another embodiment, the biomarkers of the present invention can be measured by immunoassay. Immunoassay requires biospecific capture reagents, such as antibodies, to capture the biomarkers. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art.

The present invention contemplates traditional immunoassays including, for example, sandwich immunoassays including ELISA or fluorescence-based immunoassays, as well as other enzyme immunoassays. Nephelometry is an assay performed in liquid phase, in which antibodies are in solution. Binding of the antigen to the antibody results in changes in absorbance, which is measured. In the SELDI-based immunoassay, a biospecific capture reagent for the biomarker is attached to the surface of an MS probe, such as a pre-activated ProteinChip array. The biomarker is then specifically captured on the biochip through this reagent, and the captured biomarker is detected by mass spectrometry. The Quantikine immunoassay developed by R&D Systems, Inc. (Minneapolis, Minn.) may also be used in the methods of the present invention.

C. Detection by Electrochemicaluminescent Assay

In several embodiments, the B1,4GalT-V biomarker and other biomarkers may be detected by means of an electrochemicaluminescent assay developed by Meso Scale Discovery (Gaithersburg, Md.). Electrochemiluminescence detection uses labels that emit light when electrochemically stimulated. Background signals are minimal because the stimulation mechanism (electricity) is decoupled from the signal (light). Labels are stable, non-radioactive and offer a choice of convenient coupling chemistries. They emit light at ~620 nm, eliminating problems with color quenching. See U.S. Pat. No. 7,497,997; No. 7,491,540; No. 7,288,410; No. 7,036,946; No. 7,052,861; No. 6,977,722; No. 6,919,173; No. 6,673,533; No. 6,413,783; No. 6,362,011; No. 6,319,670; No. 6,207,369; No. 6,140,045; No. 6,090,545; and No. 5,866,434. See also U.S. Patent Applications Publication No. 2009/0170121; No. 2009/006339; No. 2009/0065357; No. 2006/0172340; No. 2006/0019319; No. 2005/0142033; No. 2005/0052646; No. 2004/0022677; No. 2003/0124572; No. 2003/0113713; No. 2003/0003460; No. 2002/0137234; No. 2002/0086335; and No. 2001/0021534.

D. Other Methods for Detecting Biomarkers

The biomarkers of the present invention can be detected by other suitable methods. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Furthermore, a sample may also be analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there. Protein biochips are biochips adapted for the capture of polypeptides. Many protein biochips are described in the art. These include, for example, protein biochips produced by Ciphergen Biosystems, Inc. (Fremont, Calif.), Zyomyx (Hayward, Calif.), Invitrogen (Carlsbad, Calif.), Biacore (Uppsala, Sweden) and Procognia (Berkshire, UK). Examples of such protein biochips are described in the following patents or published patent applications: U.S. Pat. No. 6,537,749; U.S. Pat. No. 6,329,209; U.S. Pat. No. 6,225,047; U.S. Pat. No. 5,242,828; PCT International Publication No. WO 00/56934; and PCT International Publication No. WO 03/048768.

D. Sample Preparation

In several embodiments of the present invention, a blood sample is tested for the presence or absence of one or more biomarkers including B1,4GalT-V. The step of collecting a sample such as a blood sample from a subject can be carried out by phlebotomy or any other suitable technique. The blood sample may be further processed to provide a serum sample or other suitable blood fraction, such as plasma.

In alternative embodiments of the present invention, a tissue sample may be taken and tested for the presence or absence of one or more biomarkers including B1,4GalT-V. Tissue or cell samples can be removed from almost any part of the body. The most appropriate method for obtaining a tissue sample depends on the type of cancer that is suspected or diagnosed. In particular, biopsy methods include needle (e.g. fine needle aspiration), endoscopic, and excisional. Variations of these methods and the necessary devices used in such methods are known to those of ordinary skill in the art.

In other embodiments of the present invention, a stool sample may be taken and tested for the presence or absence of one or more biomarkers including B1,4GalT-V. The stool sample may be processed using techniques known to those of ordinary skill in the art. For example, the processing of the stool sample may be accomplished using an extraction buffer that is optimized for the task. An extraction buffer may be optimized to accommodate a single biomarker or multiple biomarkers of interest. An extraction buffer may fulfill any or all of the following: (1) it should liberate the analyte of interest from the stool matrix; (2) it should stabilize the free analyte; and (3) it should minimize the interference of the stool matrix in the subsequent detection of the analyte. In a specific embodiment, the extraction buffer may contain urea to improve the homogenization and extraction of the stool sample. In other embodiments, nitrilotriacetic acid or citrate may be used as chelators in a stool extraction buffer.

An optimized extraction buffer may be used in combination with a tailor-made stool sampling device. Briefly, an individual collects a defined amount of stool sample and transfers it directly into the collection device prefilled with the stabilizing extraction buffer. This convenient mode of sampling and extraction enables the transport of the specimen to a diagnostic laboratory without degradation of the analyte. Because the extraction of the stool sample can be achieved directly in the sampling device, the necessary handling and transfer procedures are reduced.

Several recent developments have focused on devices that facilitate the sampling and handling of a stool sample. EP 1 366 715 discloses a special collection tube for collection of a stool sample. The device allows for the convenient handling of a defined quantity of a stool sample and has the advantage that after appropriate extraction, the tube may be directly placed into the sample-holder of an automatic analyzer. Another example of a sophisticated stool sampling device that is appropriate for a convenient sampling and handling of a stool sample is described in WO 03/068398.

The stool sample may be used or processed directly after sampling or stored cooled or stored frozen. Frozen stool samples can be processed by thawing, followed by dilution in an appropriate buffer, mixing and centrifugation. Supernatants may be used as liquid sample for subsequent measurement of the biomarkers.

IV. Determination of Subject Cancer Status

A. B1,4GalT-V Biomarker

The biomarkers of the present invention can be used in diagnostic tests to assess cancer status in a subject, e.g., to diagnose cancer. The phrase "cancer status" includes any distinguishable manifestation of the disease, including non-disease. For example, disease status includes, without limitation, the presence or absence of disease (e.g., cancer v. non-cancer), the risk of developing disease, the stage of the disease, the progress of disease (e.g., progress of disease or remission of disease over time) and the effectiveness or response to treatment of disease. Based on this status, further procedures may be indicated, including additional diagnostic tests or therapeutic procedures or regimens. For ease of reference, although the B1,4GalT-V biomarker is useful in the treatment of cancer, it may be referred to specifically as being useful in the treatment of colorectal cancer. A reference to the use of the B1,4GalT-V biomarker in colorectal cancer shall be understood to mean colorectal cancer and other cancers as well.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the B1,4GalT-V biomarker of the present invention may show a statistical difference in different cancer statuses of at least $p<0.05$, $p<10^{-2}$, $p<10^{-3}$, $p<10^{-4}$ or $p<10^{-5}$. Diagnostic tests that use this biomarker alone or in combination with other known biomarkers may show a sensitivity and specificity of at least 75%, at least 80%, at least 85%, at least 90%, at least 95%, at least 98% and about 100%. In a specific embodiment, the sensitivity and specificity is at least 68%.

The B1,4GalT-V biomarker is differentially present in colorectal cancer, and, therefore, is useful in aiding in the determination of colorectal cancer status. In specific embodiments, the biomarker is measured in a subject sample using the methods described herein. The measurement may then be compared with a diagnostic amount or cut-off that distinguishes a positive colorectal cancer status from a negative colorectal cancer status. The diagnostic amount represents a measured amount of a biomarker above which or below which a subject is classified as having a particular colorectal cancer status. For example, if the biomarker is up-regulated compared to normal during colorectal cancer, then a measured amount above the diagnostic cutoff provides a diagnosis of colorectal cancer. Alternatively, if the biomarker is down-regulated during colorectal cancer, then a measured amount below the diagnostic cutoff provides a diagnosis of colorectal cancer. As is well understood in the art, by adjusting the particular diagnostic cut-off used in an assay, one can increase sensitivity or specificity of the diagnostic assay depending on the preference of the diagnostician. The particular diagnostic cut-off can be determined, for example, by measuring the amount of the biomarker in a statistically significant number of samples from subjects with the different colorectal cancer statuses, and drawing the cut-off to suit the desired levels of specificity and sensitivity.

B. Biomarker Panels Including B1,4GalT-V

As the skilled artisan will appreciate there are many ways to use the measurements of two or more markers in order to improve the diagnostic question under investigation. In a quite simple, but nonetheless often effective approach, a positive result is assumed if a sample is positive for at least one of the markers investigated.

Frequently, however, the combination of markers is evaluated. Preferably the values measured for markers of a marker panel, e.g., for B1,4GalT-V, ASC, CYFRA 21-1 and NSE, are mathematically combined and the combined value is correlated to the underlying diagnostic question. Biomarker values may be combined by any appropriate state of the art mathematical method. Well-known mathematical methods for correlating a marker combination to a disease employ methods like discriminant analysis (DA) (e.g., linear-, quadratic-, regularized-DA), Kernel Methods (e.g., SVM), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present invention. In one embodiment, the method used in correlating biomarker combination of the present invention e.g. to the absence or presence of cancer is selected from DA (e.g., Linear-, Quadratic-, Regularized Discriminant Analysis), Kernel Methods (e.g., SVM), Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression). Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

B. Determining Risk of Developing Disease

In a specific embodiment, the present invention provides methods for determining the risk of developing disease in a subject. Biomarker amounts or patterns are characteristic of various risk states, e.g., high, medium or low. The risk of developing a disease is determined by measuring the relevant biomarker or biomarkers and then either submitting them to a classification algorithm or comparing them with a reference amount and/or pattern of biomarkers that is associated with the particular risk level.

C. Determining Stage of Disease

In another embodiment, the present invention provides methods for determining the stage of disease in a subject. Each stage of the disease has a characteristic amount of a biomarker or relative amounts of a set of biomarkers (a pattern). The stage of a disease is determined by measuring the relevant biomarker or biomarkers and then either submitting them to a classification algorithm or comparing them with a reference amount and/or pattern of biomarkers that is associated with the particular stage.

D. Determining Course (Progression/Remission) of Disease

In one embodiment, the present invention provides methods for determining the course of disease in a subject. Disease course refers to changes in disease status over time, including disease progression (worsening) and disease regression (improvement). Over time, the amounts or relative amounts (e.g., the pattern) of the biomarker(s) changes. For example, biomarker B1,4GalT-V is increased with colorectal cancer, while biomarker "X" may be decreased in colorectal cancer. Therefore, the trend of these biomarkers, either increased or decreased over time toward diseased or non-diseased indicates the course of the disease. Accordingly, this method involves measuring one or more biomarkers in a subject at least two different time points, e.g., a first time and a second time, and comparing the change in amounts, if any. The course of disease is determined based on these comparisons.

E. Subject Management

In certain embodiments of the methods of qualifying colorectal cancer status, the methods further comprise managing subject treatment based on the status. Such management includes the actions of the physician or clinician subsequent to determining colorectal cancer status. For example, if a physician makes a diagnosis of colorectal cancer, then a certain regime of treatment, such as prescription or administration of therapeutic agent might follow. Alternatively, a diagnosis of non-colorectal cancer might be followed with further testing to determine a specific disease that the patient might be suffering from. Also, further tests may be called for if the diagnostic test gives an inconclusive result on colorectal cancer status.

F. Determining Therapeutic Efficacy of Pharmaceutical Drug

In another embodiment, the present invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of one or more of the biomarkers of the present invention may change toward a non-disease profile. Therefore, one can follow the course of the amounts of one or more biomarkers in the subject during the course of treatment. Accordingly, this method involves measuring one or more biomarkers (including B1,4GalT-V) in a subject receiving drug therapy, and correlating the amounts of the biomarkers with the disease status of the subject. One embodiment of this method involves determining the levels of one or more biomarkers at least two different time points during a course of drug therapy, e.g., a first time and a second time, and comparing the change in amounts of the biomarkers, if any. For example, the one or more biomarkers can be measured before and after drug administration or at two different time points during drug administration. The effect of therapy is determined based on these comparisons. If a treatment is effective, then one or more biomarkers will trend toward normal, while if treatment is ineffective, the one or more biomarkers will trend toward disease indications. If a treatment is effective, then the one or more biomarkers will trend toward normal, while if treatment is ineffective, the one or more biomarkers will trend toward disease indications.

G. Generation of Classification Algorithms for Qualifying Colorectal Cancer Status In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition (e.g., diseased versus non-diseased).

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART-classification and regression trees), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al. "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows™ or Linux™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

The learning algorithms described above are useful both for developing classification algorithms for the biomarkers already discovered, or for finding new biomarkers. The classification algorithms, in turn, form the base for diagnostic tests by providing diagnostic values (e.g., cut-off points) for biomarkers used singly or in combination.

H. Kits for the Detection of Cancer Biomarkers

In another aspect, the present invention provides kits for qualifying cancer status, which kits are used to detect the B1,4GalT-V biomarker and optionally other cancer biomarkers. In a specific embodiment, the kit is provided as an ELISA kit comprising an antibody to B1,4GalT-V. The ELISA kit may comprise a solid support, such as a chip, microtiter plate (e.g., a 96-well plate), bead, or resin having a B1,4GalT-V capture reagent attached thereon. The kit may further comprise a means for detecting B1,4GalT-V, such as an anti-B1,4GalT-V antibody, and a secondary antibody-signal complex such as horseradish peroxidase (HRP)-conjugated goat anti-rabbit IgG antibody and tetramethyl benzidine (TMB) as a substrate for HRP.

The kit for qualifying cancer status may be provided as an immuno-chromatography strip comprising a membrane on which B1,4GalT-V antibody is immobilized, and a means for detecting B1,4GalT-V, e.g., a gold particle bound B1,4GalT-V antibody, where the membrane, includes NC membrane and PVDF membrane. The kit may comprise a plastic plate on which a sample application pad, a gold particle bound B1,4GalT-V antibody temporally immobilized on a glass fiber filter, a nitrocellulose membrane on which a B1,4GalT-V antibody band and a secondary antibody band are immobilized and an absorbent pad are positioned in a serial manner, so as to keep continuous capillary flow of blood serum.

A cancer patient can be diagnosed by adding blood or blood serum from the patient to the kit and detecting B1,4GalT-V conjugated with B1,4GalT-V antibody, specifically, by a method which comprises the steps of: (i) collecting blood or blood serum from the patient; (ii) separating blood serum from the patient's blood; (iii) adding the blood serum from patient to a diagnostic kit; and, (iv) detecting B1,4GalT-V conjugated with B1,4GalT-V antibody. In this method, the B1,4GalT-V antibodies are brought into contact with the patient's blood. If B1,4GalT-V is present in the sample, the B1,4GalT-V antibodies will bind to the sample, or a portion thereof. In other kit and diagnostic embodiments, blood or blood serum need not be collected from the patient (i.e., it is already collected). Moreover, in other embodiments, the sample may comprise a tissue biopsy sample.

The kit can also comprise a washing solution or instructions for making a washing solution, in which the combination of the capture reagent and the washing solution allows capture of the biomarker or biomarkers on the solid support for subsequent detection by, e.g., an antibody or mass spectrometry. In a further embodiment, a kit can comprise instructions for suitable operational parameters in the form of a label or separate insert. For example, the instructions may inform a consumer about how to collect the sample, how to wash the probe or the particular biomarkers to be detected. In yet another embodiment, the kit can comprise one or more containers with biomarker samples, to be used as standard(s) for calibration.

V. Treatment of Cancer by Targeting B1,4GALT-V

The present invention generally relates to the treatment and management of cancer by targeting B1,4GalT-V. In one aspect, the present invention relates to inhibiting the expression of B1,4GalT-V Inhibition may be achieved by impeding any steps in the replication, transcription, splicing or translation of the B1,4GalT-V gene. The sequence of B1,4GalT-V is disclosed in GenBank Accession No. AF038663 (SEQ. ID NO. 1), the entirety of which is incorporated herein by reference. In another aspect, the present invention relates to interfering, inhibiting, or otherwise preventing the functional aspects of the B1,4GalT-V protein.

With regard to disease state, the compositions of the present invention are useful in treating and/or preventing cancer including, but not limited to, colon, lung, liver, prostate, ovarian, breast, brain, thyroid, bone, kidney/renal and skin (e.g., melanoma) cancers, as well as cancers such as leukemia and lymphoma. Further, more specific examples of cancer include, but are not limited to, malignant and non-malignant cell growth, leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignant lymphoma, non-hodgkin's lymphoma, Burkitt's lymphoma, multiple myeloma, Kaposi's sarcoma, colorectal carcinoma, pancreatic carcinoma, nasopharyngeal carcinoma, neural blastoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain, and the like.

In a specific embodiment, the methods and compositions of the present invention may be used to treat a primary tumor. In another embodiment, the methods and compositions of the present invention may be used to treat or prevent metastasis. In yet another embodiment, the methods and compositions of the present invention may be used to treat a secondary tumor. In an alternative embodiment, the methods and compositions of the present invention may be used to treat or prevent colon cancer. In a particular embodiment, the methods and compositions of the present invention may be used to treat or prevent renal cancer. In a specific embodiment, the methods and compositions of the present invention may be used to treat or prevent pancreatic cancer. In several embodiments, the methods and compositions of the present invention may be used to treat or prevent any cancer in which B1,4GalT-V is overexpressed.

A. RNA Interference Compositions for Targeting B1,4GALT-V mRNA

In one aspect of the present invention, the expression of B1,4GalT-V may be inhibited by the use of RNA interference techniques (RNAi). RNAi is a remarkably efficient process whereby double-stranded RNA (dsRNA) induces the sequence-specific degradation of homologous mRNA in animals and plant cells. See Hutvagner and Zamore, 12 CURR. OPIN. GENET. DEV. 225-32 (2002); Hammond et al., 2 NATURE REV. GEN. 110-19 (2001); Sharp, 15 GENES DEV. 485-90 (2001). RNAi can be triggered, for example, by nucleotide (nt) duplexes of small interfering RNA (siRNA) (Chiu et al., 10 MOL. CELL. 549-61 (2002); Elbashir et al., 411 Nature 494-98 (2001)), micro-RNAs (miRNA), functional small-hairpin RNA (shRNA), or other dsRNAs which are expressed in-vivo using DNA templates with RNA polymerase III promoters. See, e.g., Zeng et al., 9 MOL. CELL. 1327-33 (2002); Paddison et al., 16 GENES DEV. 948-58 (2002); Lee et al., 20 NATURE BIOTECHNOL. 500-05 (2002); Paul et al., 20 NATURE BIOTECHNOL. 505-08 (2002); Tuschl, 20 NATURE BIOTECHNOL. 440-48 (2002); Yu et al., 99 (9) PROC. NATL. ACAD. SCI. USA, 6047-52 (2002); McManus et al., 8 RNA 842-50 (2002); Sui et al., 99 (6) PROC. NATL. ACAD. SCI. USA 5515-20 (2002).

i. Small Interfering RNA

In particular embodiments, the present invention features "small interfering RNA molecules" ("siRNA molecules" or "siRNA"), methods of making siRNA molecules and methods for using siRNA molecules (e.g., research and/or therapeutic methods). The siRNAs of this invention encompass any siRNAs that can modulate the selective degradation of B1,4GalT-V mRNA.

In a specific embodiment, the siRNA of the present invention may comprise double-stranded small interfering RNA molecules (ds-siRNA). A ds-siRNA molecule of the present invention may be a duplex made up of a sense strand and a complementary antisense strand, the antisense strand being sufficiently complementary to a target B1,4GalT-V mRNA to mediate RNAi. The siRNA molecule may comprise about 10 to about 50 or more nucleotides. More specifically, the siRNA molecule may comprise about 16 to about 30, e.g., 16, 17, 18, 19, 20, 21, 22, 23, 24, 25, 26, 27, 28, 29, or 30 nucleotides in each strand. The strands may be aligned such that there are at least 1, 2, or 3 bases at the end of the strands which do not align (e.g., for which no complementary bases occur in the opposing strand) such that an overhang of 1, 2 or 3 residues occurs at one or both ends of the duplex when strands are annealed.

In an alternative embodiment, the siRNA of the present invention may comprise single-stranded small interfering RNA molecules (ss-siRNA). Similar to the ds-siRNA molecules, the ss-siRNA molecule may comprise about 10 to about 50 or more nucleotides. More specifically, the ss-siRNA molecule may comprise about 15 to about 45 or more nucleotides. Alternatively, the ss-siRNA molecule may comprise about 19 to about 40 nucleotides. The ss-siRNA molecules of the present invention comprise a sequence that is "sufficiently complementary" to a target mRNA sequence to direct target-specific RNA interference (RNAi), as defined herein, e.g., the ss-siRNA has a sequence sufficient to trigger the destruction of the target mRNA by the RNAi machinery or process. In one embodiment, the ss-siRNA molecule can be designed such that every residue is complementary to a residue in the target molecule. Alternatively, substitutions can be made within the molecule to increase stability and/or enhance processing activity of the molecule. Substitutions can be made within the strand or can be made to residues at the ends of the strand. In a specific embodiment, the 5'-terminus may be phosphorylated (e.g., comprises a phosphate, diphosphate, or triphosphate group). In another embodiment, the 3' end of an siRNA may be a hydroxyl group in order to facilitate RNAi, as there is no requirement for a 3' hydroxyl group when the active agent is a ss-siRNA molecule. In other instances, the 3' end (e.g., C3 of the 3' sugar) of ss-siRNA molecule may lack a hydroxyl group (e.g., ss-siRNA molecules lacking a 3' hydroxyl or C3 hydroxyl on the 3' sugar (e.g., ribose or deoxyribose).

In another aspect, the siRNA molecules of the present invention may be modified to improve stability under in vitro and/or in vivo conditions, including, for example, in serum and in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference. For example, the absence of a 2' hydroxyl may significantly enhance the nuclease resistance of the siRNAs in tissue culture medium.

Furthermore, the siRNAs of the present invention may include modifications to the sugar-phosphate backbone or nucleosides. These modifications can be tailored to promote selective genetic inhibition, while avoiding a general panic response reported to be generated by siRNA in some cells. In addition, modifications can be introduced in the bases to protect siRNAs from the action of one or more endogenous enzymes.

In an embodiment of the present invention, the siRNA molecule may contain at least one modified nucleotide analogue. The nucleotide analogues may be located at positions where the target-specific activity, e.g., the RNAi mediating activity is not substantially effected, e.g., in a region at the 5'-end and/or the 3'-end of the RNA molecule. Particularly, the ends may be stabilized by incorporating modified nucleotide analogues. Examples of nucleotide analogues include sugar- and/or backbone-modified ribonucleotides (e.g., include modifications to the phosphate-sugar backbone). For example, the phosphodiester linkages of natural RNA may be modified to include at least one of a nitrogen or sulfur heteroatom. In backbone-modified ribonucleotides, the phosphoester group connecting to adjacent ribonucleotides may be replaced by a modified group, e.g., a phosphothioate group. In sugar-modified ribonucleotides, the 2' OH-group may be replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Nucleobase-modified ribonucleotides may also be utilized, e.g., ribonucleotides containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

Derivatives of siRNAs may also be utilized herein. For example, crosslinking can be employed to alter the pharmacokinetics of the composition, e.g., to increase half-life in the body. Thus, the present invention includes siRNA derivatives that include siRNA having two complementary strands of nucleic acid, such that the two strands are crosslinked. The present invention also includes siRNA derivatives having a non-nucleic acid moiety conjugated to its 3' terminus (e.g., a peptide), organic compositions (e.g., a dye), or the like. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The siRNAs of the present invention can be enzymatically produced or totally or partially synthesized. Moreover, the siRNAs can be synthesized in vivo or in vitro. For siRNAs that are biologically synthesized, an endogenous or a cloned exogenous RNA polymerase may be used for transcription in vivo, and a cloned RNA polymerase can be used in vitro. siRNAs that are chemically or enzymatically synthesized are preferably purified prior to the introduction into the cell.

Although one hundred percent (100%) sequence identity between the siRNA and the target region is preferred in particular embodiments, it is not required to practice the invention. siRNA molecules that contain some degree of modification in the sequence can also be adequately used for the purpose of this invention. Such modifications may include, but are not limited to, mutations, deletions or insertions, whether spontaneously occurring or intentionally introduced.

Moreover, not all positions of a siRNA contribute equally to target recognition. In certain embodiments, for example, mismatches in the center of the siRNA may be critical and could essentially abolish target RNA cleavage. In other embodiments, the 3' nucleotides of the siRNA do not contribute significantly to specificity of the target recognition. In particular, residues 3' of the siRNA sequence which is complementary to the target RNA (e.g., the guide sequence) may not critical for target RNA cleavage.

Sequence identity may be determined by sequence comparison and alignment algorithms known to those of ordinary skill in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (e.g., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (e.g., a local alignment). A non-limiting example of a local alignment algorithm utilized for the comparison of sequences is the algorithm of Karlin and Altschul, 87 PROC. NATL. ACAD. SCI. USA 2264-68 (1990), and as modified as in Karlin and Altschul 90 PROC. NATL. ACAD. SCI. USA 5873-77 (1993). Such an algorithm is incorporated into the BLAST programs (version 2.0) of Altschul, et al., 215 J. MOL. BIOL. 403-10 (1990).

In another embodiment, the alignment may optimized by introducing appropriate gaps and determining percent identity over the length of the aligned sequences (e.g., a gapped alignment). To obtain gapped alignments for comparison purposes, Gapped BLAST can be utilized as described in Altschul et al., 25 (17) NUCLEIC ACIDS RES. 3389-3402 (1997). In another embodiment, the alignment may be optimized by introducing appropriate gaps and determining percent identity over the entire length of the sequences aligned (e.g., a global alignment). A non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

In particular embodiments, greater than 90% sequence identity, e.g., 91%, 92%, 93%, 94%, 95%, 96%, 97%, 98%, 99% or even 100% sequence identity, between the siRNA and the portion of the target gene may be used. Alternatively, the siRNA may be defined functionally as a nucleotide sequence (or oligonucleotide sequence) that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing). Additional hybridization conditions include, but are not limited to, hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length can be about 5-10° C. less than the melting temperature (Tm) of the hybrid, where Tm is determined according to the following equations. For hybrids less than 18 base pairs in length, $Tm(° C.)=2(\# of A+T bases)+4(\# of G+C bases)$. For hybrids between 18 and 49 base pairs in length, $Tm(° C.)=81.5+16.6(\log 10[Na^+])+0.41(\% G+C)-(600/N)$, where N is the number of bases in the hybrid, and [$Na^+$] is the concentration of sodium ions in the hybridization buffer ([$Na^+$] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference. The length of the identical nucleotide sequences may be at least about 10, 12, 15, 17, 20, 22, 25, 27, 30, 32, 35, 37, 40, 42, 45, 47 50 or more bases.

ii. Other Compositions for Targeting B1,4GalT-V DNA or mRNA

Antisense molecules can act in various stages of transcription, splicing and translation to block the expression of a target gene. Without being limited by theory, antisense molecules can inhibit the expression of a target gene by inhibiting transcription initiation by forming a triple strand, inhibiting transcription initiation by forming a hybrid at an RNA polymerase binding site, impeding transcription by hybridizing with an RNA molecule being synthesized, repressing splicing by hybridizing at the junction of an exon and an intron or at the spliceosome formation site, blocking the translocation of an mRNA from nucleus to cytoplasm by hybridization, repressing translation by hybridizing at the translation initiation factor binding site or ribosome biding site, inhibiting peptide chain elongation by hybridizing with the coding region or polysome binding site of an mRNA, or repressing gene expression by hybridizing at the sites of interaction between nucleic acids and proteins. An example of an antisense oligonucleotide of the present invention is a cDNA that, when introduced into a cancer cell, transcribes into an RNA molecule having a sequence complementary to at least part of the B1,4GalT-V mRNA.

Furthermore, antisense oligonucleotides of the present invention include oligonucleotides having modified sugar-phosphodiester backbones or other sugar linkages, which can provide stability against endonuclease attacks. The present invention also encompasses antisense oligonucleotides that are covalently attached to an organic or other moiety that increase their affinity for a target nucleic acid sequence. For example, intercalating agents, alkylating agents, and metal complexes can be also attached to the antisense oligonucleotides of the present invention to modify their binding specificities.

The present invention also provides ribozymes as a tool to inhibit B1,4GalT-V expression. Ribozymes are enzymatic RNA molecules capable of catalyzing the specific cleavage of RNA. The characteristics of ribozymes are well-known in the art. See, e.g., Rossi, 4 CURRENT BIOLOGY 469-71 (1994). Without being limited by theory, the mechanism of ribozyme action involves sequence specific hybridization of the ribozyme molecule to complementary target RNA, followed by an endonucleolytic cleavage. In particular embodiments, the ribozyme molecules include one or more sequences complementary to the target gene mRNA, and include the well known catalytic sequence responsible for mRNA cleavage. See U.S. Pat. No. 5,093,246. Using the known sequence of the target B1,4GalT-V mRNA, a restriction enzyme-like ribozyme can be prepared using standard techniques.

The expression of the B1,4GalT-V gene can also be inhibited by using triple helix formation. Nucleic acid molecules to be used in triple helix formation for the inhibition of transcription can be single stranded and composed of deoxynucleotides. The base composition of these oligonucleotides must be designed to promote triple helix formation via Hoogsteen base paring rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarity to a purine-rich region of a single strand of the duplex in a parallel orientation to that strand. In addition, nucleic acid molecules that are purine-rich, e.g., containing a stretch of G residues, may be chosen. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so-called "switchback" nucleic acid molecule. Switchback molecules are synthesized in an alternating 5'-3',3'-5' manner, such that they base pair first with one strand of a duplex and then the other, eliminating the necessity for a sizeable stretch of either purines or pyrimidines to be present on one strand of a duplex.

The expression of B1,4GalT-V may be also inhibited by what is referred to as "co-repression." Co-repression refers to the phenomenon in which, when a gene having an identical or similar to the target sequence is introduced to a cell, expression of both introduced and endogenous genes becomes repressed. This phenomenon, although first observed in plant system, has been observed in certain animal systems as well. The sequence of the gene to be introduced does not have to be identical to the target sequence, but sufficient homology allows the co-repression to occur. The determination of the extent of homology depends on individual cases, and is within the ordinary skill in the art.

It would be readily apparent to one of ordinary skill in the art that other methods of gene expression inhibition that selectively target a B1,4GalT-V DNA or mRNA can also be used in connection with this invention without departing from the spirit of the invention. In a specific embodiment, using techniques known to those of ordinary skill in the art, the present invention contemplates affecting the promoter region of B1,4GalT-V (which is regulated by Sp-1) to effectively switch off transcription.

iii. Design and Production of the RNAi Compositions

One or more of the following guidelines may be used in designing the sequence of siRNA and other nucleic acids designed to bind to a target mRNA, e.g., shRNA, stRNA, antisense oligonucleotides, ribozymes, and the like, that are advantageously used in accordance with the present invention.

Beginning with the AUG start codon of B1,4GalT-V gene, each AA dinucleotide sequence and the 3' adjacent 16 or more nucleotides are potential siRNA targets. In a specific embodiment, the siRNA is specific for a target region that differs by at least one base pair between the wild type and mutant allele or between splice variants. In dsRNAi, the first strand is complementary to this sequence, and the other strand identical or substantially identical to the first strand. siRNAs with lower G/C content (35-55%) may be more active than those with G/C content higher than 55%. Thus in one embodiment, the invention includes nucleic acid molecules having 35-55% G/C content. In addition, the strands of the siRNA can be paired in such a way as to have a 3' overhang of 1 to 4, e.g., 2, nucleotides. Thus in another embodiment, the nucleic acid molecules may have a 3' overhang of 2 nucleotides, such as TT. The overhanging nucleotides may be either RNA or DNA. In one embodiment, it may be desirable to choose a target region wherein the mismatch is a purine:purine mismatch.

Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website (http://www.ncbi.nih.gov). Select one or more sequences that meet the criteria for evaluation.

Another method includes selecting in the sequence of the target mRNA, a region located from about 50 to about 100 nt 3' from the start codon. In this region, search for the following sequences: AA(N19)TT or AA(N21), where N=any nucleotide. The GC content of the selected sequence should be from about 30% to about 70%, preferably about 50%. To maximize the specificity of the RNAi, it may be desirable to use the selected sequence in a search for related sequences in the genome of interest; sequences absent from other genes are preferred. The secondary structure of the target mRNA may be determined or predicted, and it may be preferable to select a region of the mRNA that has little or no secondary structure, but it should be noted that secondary structure seems to have little impact on RNAi. When possible, sequences that bind transcription and/or translation factors should be avoided, as they might competitively inhibit the binding of a siRNA, sbRNA or stRNA (as well as other antisense oligonucleotides) to the mRNA. Further general information about the design and use of siRNA may be found in "The siRNA User Guide," available at The Max-Planck-Institut fur Biophysikalishe Chemie website (http://www.mpibpc.mpg.de).

Negative control siRNAs should have the same nucleotide composition as the selected siRNA, but without significant sequence complementarity to the appropriate genome. Such negative controls may be designed by randomly scrambling the nucleotide sequence of the selected siRNA; a homology search can be performed to ensure that the negative control lacks homology to any other gene in the appropriate genome.

iv. Delivery of B1,4GalT-V RNA Targeting Compositions

Delivery of the compositions of the present invention (e.g., siRNAs, antisense oligonucleotides, or other compositions described herein) into a patient can either be direct, e.g., the patient is directly exposed to the compositions of the present invention or compound-carrying vector, or indirect, e.g., cells are first transformed with the compositions of this invention in vitro, then transplanted into the patient for cell replacement therapy. These two approaches are known as in vivo and ex vivo therapy, respectively.

In the case of in vivo therapy, the compositions of the present invention are directly administered in vivo, where they are expressed to produce the encoded product. This can be accomplished by any of numerous methods known in the art, e.g., by constructing them as part of an appropriate nucleic acid expression vector and administering them so that they become intracellular, by infection using a defective or attenuated retroviral or other viral vector, by direct injection of naked DNA, by coating with lipids or cell-surface receptors or transfecting agents, encapsulation in liposomes, nanoparticles, microparticles, or microcapsules, by administering them in linkage to a peptide which is known to enter the cell or nucleus, or by administering them in linkage to a ligand subject to receptor-mediated endocytosis which can be used to target cell types specifically expressing the receptors. Further, the compositions of the present invention can be targeted in vivo for cell specific uptake and expression, by targeting a specific receptor. See, e.g., WO93/14188, WO 93/20221, WO 92/22635, WO92/20316, and WO 92/06180.

Ex vivo therapy involves transferring the compositions of the present invention to cells in tissue culture by methods well-known in the art such as electroporation, transfection, lipofection, microinjection, calcium phosphate mediated transfection, cell fusion, chromosome-mediated gene transfer, microcell-mediated gene transfer, spheroplast fusion, and infection with a viral vector containing the nucleic acid sequences. These techniques should provide for the stable transfer of the compositions of this invention to the cell, so that they are expressible by the cell and preferably heritable and expressible by its cell progeny. In particular embodiments, the method of transfer includes the transfer of a selectable marker to the cells. The cells are then placed under selection to isolate those cells that have taken up and are expressing the transferred compositions. The resulting recombinant cells can be delivered to a patient by various methods known in the art. Examples of the delivery methods include, but are not limited to, subcutaneous injection, skin graft, and intravenous injection.

B. Antibodies to B1,4GalT-V

The present invention contemplates the use of antibodies specific for B1,4GalT-V in the treatment and prevention of cancer. The phrases "binding specificity," "binding specifically to, "specific binding" or otherwise any reference to an antibody to B1,4GalT-V, refers to a binding reaction that is determinative of the presence of the corresponding B1,4GalT-V antigen to the antibody in a heterogeneous population of antigens and other biologics. The parameters required to achieve such specificity can be determined routinely, using conventional methods in the art including, but not limited to, competitive binding studies. The binding affinity of an antibody can also be readily determined, for example, by Scatchard analysis (Scatchard, Ann. NY Acad. Sci. 51: 660-672, 1949). In some embodiments, the immunoglobulins of the present invention bind to B1,4GalT-V at least about 5, at least about 10, at least about 100, at least about $10^3$, at least about $10^4$, at least $10^5$, and at least $10^6$ fold higher than to other proteins.

Various procedures known in the art may be used for the production of antibodies to B1,4GalT-V, B1,4GalT-V family members or any subunit thereof, or B1,4GalT-V, or a fragment, derivative, homolog or analog of the protein. Antibodies of the present invention include, but are not limited to, synthetic antibodies, polyclonal antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv) (including bi-specific scFvs), single chain antibodies Fab fragments, F(ab') fragments, disulfide-linked Fvs (sdFv), and anti-idiotypic (anti-Id) antibodies, and epitope-binding fragments of any of the above. In particular, antibodies of the present invention include immunoglobulin molecules and immunologically active portions of immunoglobulin molecules, e.g., molecules that contain an antigen binding site that immunospecifically binds to an antigen (e.g., one or more complementarity determining regions (CDRs) of an antibody).

Another embodiment for the preparation of antibodies according to the invention is the use of peptide mimetics. Mimetics are peptide-containing molecules that mimic elements of protein secondary structure. See, for example, Johnson et al., "Peptide Turn Mimetics" in BIOTECHNOLOGY AND PHARMACY, Pezzuto et al., Eds., Chapman and Hall, New York (1993). The underlying rationale behind the use of peptide mimetics in rational design is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used to engineer second generation molecules having many of the natural properties of the targeting antibodies disclosed herein, but with altered and even improved characteristics. More specifically, under this rational design approach, peptide mapping may be used to determine "active" antigen recognition residues, and along with molecular modeling and molecular dynamics trajectory analysis, peptide mimic of the antibodies containing antigen contact residues from multiple CDRs may be prepared.

In some embodiments, an antibody specifically binds an epitope of the B1,4GalT-V protein. It is to be understood that the peptide regions may not necessarily precisely map one epitope, but may also contain B1,4GalT-V sequence that is not immunogenic. Methods of predicting other potential epitopes to which an immunoglobulin of the invention can bind are well-known to those of skill in the art and include, without limitation, Kyte-Doolittle Analysis (Kyte, J. and Dolittle, R. F., 157 J. MOL. BIOL. 105-32 (1982)); Hopp and Woods Analysis (Hopp, T. P. and Woods, K. R., 78 PROC. NATL. ACAD. SCI. USA 3824-28 (1981); Hopp, T. J. and Woods, K. R., 20 MOL. IMMUNOL. 483-89 (1983); Hopp, T. J., 88 J. IMMUNOL. METHODS 1-18 (1986)); Jameson-Wolf Analysis (Jameson, B. A. and Wolf, H., 4 COMPUT. APPL. BIOSCI. 181-86 (1988)); and Emini Analysis (Emini et al., 140 VIROLOGY 13-20 (1985)).

Amino acid sequence variants of the antibodies of the present invention may be prepared by introducing appropriate nucleotide changes into the polynucleotide that encodes the antibody or by peptide synthesis. Such modifications include, for example, deletions from, and/or insertions into and/or substitutions of, residues within the amino acid sequences of the antibody. Any combination of deletions, insertions, and substitutions may be made to arrive at the final construct.

Amino acid sequence insertions include amino-terminal and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody of a polypeptide that increases the serum half-life of the antibody.

Another type of antibody variant is an amino acid substitution variant. These variants have at least one amino acid residue in the antibody molecule replaced by a different residue. For example, the sites of greatest interest for substitutional mutagenesis of antibodies include the hypervariable regions, but framework region (FR) alterations are also contemplated.

A useful method for the identification of certain residues or regions of the B1,4GalT-V antibodies that are preferred locations for substitution, i.e., mutagenesis, is alanine scanning mutagenesis. See Cunningham & Wells, 244 SCIENCE 1081-85 (1989). Briefly, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. The amino acid locations demonstrating functional sensitivity to the substitutions are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis may be conducted at the target codon or region and the expressed antibody variants screened for the desired activity.

Substantial modifications in the biological properties of the antibody can be accomplished by selecting substitutions that differ significantly in their effect on, maintaining (i) the structure of the polypeptide backbone in the area of the substitution, for example, as a sheet or helical conformation, (ii) the charge or hydrophobicity of the molecule at the target site, or (iii) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Conservative substitutions involve exchanging of amino acids within the same class.

Any cysteine residue not involved in maintaining the proper conformation of the antibody also may be substituted, generally with serine, to improve the oxidative stability of the molecule and prevent aberrant crosslinking Conversely, cysteine bond(s) may be added to the antibody to improve its stability, particularly where the antibody is an immunoglobulin fragment such as an Fv fragment.

Another type of substitutional variant involves substituting one or more hypervariable region residues of a parent antibody. Generally, the resulting variant(s), i.e., functional equivalents as defined above, selected for further development will have improved biological properties relative to the parent antibody from which they are generated. A convenient way for generating such substitutional variants is by affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed.

In order to identify candidate hypervariable region sites for modification, alanine-scanning mutagenesis may be performed to identify hypervariable region residues contributing significantly to antigen binding. Alternatively, or additionally, it may be beneficial to analyze a crystal structure of the antibody-antigen complex to identify contact points between the antibody and antigen. Such contact residues and neighboring residues are candidates for substitution according to the techniques elaborated herein. Once generated, the panel of variants is subjected to screening as described herein and antibodies with superior properties in one or more relevant assays may be selected for further development.

It may be desirable to modify the antibodies of the present invention, i.e., create functional equivalents, with respect to effector function, e.g., so as to enhance antigen-dependent cell-mediated cytotoxicity (ADCC) and/or complement dependent cytotoxicity (CDC) of the antibody. This may be achieved by introducing one or more amino acid substitutions in an Fc region of an antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). Caron et al., 176 J. EXP MED. 1191-95 (1992); Shopes, 148 J. IMMUNOL. 2918-22 (1992). Homodimeric antibodies with enhanced anti-tumor activity may also be prepared using heterobifunctional cross-linkers as described in Wolff et al., 53 CANCER RESEARCH 2560-65 (1993). Alternatively, an antibody can be engineered which has dual Fc regions and may thereby have enhanced complement lysis and ADCC capabilities. Stevenson et al., 3 ANTI-CANCER DRUG DESIGN 219-30 (1989).

To increase the serum half life of an antibody, one may incorporate a salvage receptor binding epitope into the antibody (especially an immunoglobulin fragment) as described in, for example, U.S. Pat. No. 5,739,277. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Polynucleotide molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site directed) mutagenesis, PCR mutagenesis, and cassette mutagenesis of an earlier prepared variant or a non-variant version of the anti-B1, 4GalT-V antibodies of the present invention.

C. Small Molecule Inhibitors

In another aspect, the present invention provides methods and compositions for treating cancers associated with the overexpression of B1,4GalT-V. Any compound that inhibits the action of B1,4GalT-V may be used in the present invention. In one embodiment, the B1,4GalT-V may comprise D-threo-1-Phenyl-2-decanoylamino-3-morpholino-1-propanol (D-PDMP or PDMP). It is contemplated that D-PDMP can be used alone, or in combination with other known compounds including those disclosed herein, to treat or prevent cancer.

Derivatives of D-PDMP may also be used in the methods of the present invention. PDMP derivatives are compounds with structural similarity to PDMP that inhibit the function of B1,4GalT-V. Examples of PDMP derivatives including, but are not limited to, D-threo-3',4'-ethylenedioxyl-1-phenyl-2-palmitoylamino-3-pyrrolidino-1-propanol and D-threo-4'-hydroxyl-1-phenyl-2-palmitoylamino-3-pyrrolidino-1-propanol. Another D-PDMP derivative comprises 1-phenyl-2-hexadecanoylamino-3-morpholino-1-propanol (PPMP). U.S. Pat. No. 6,569,889, No. 5,707,649, and No. 5,041,441, as well as U.S. Patent Applications Publication No. 2003/0073690, No. 2002/0198240, and No. 2001/0041735, describe additional D-PDMP derivatives that may be useful with the present invention. See also U.S. Pat. No. 6,511,979, U.S. Pat. No. 6,228,889, and U.S. Pat. No. 5,972,928, and U.S. Patent Application Publication No. 2009/020439.

VI. Pharmaceutical Compositions for the Treatment of Cancer

The present invention also provides pharmaceutical compositions. Such compositions comprise a therapeutically effective amount of a B1,4GalT-V therapeutic and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the B1,4GalT-V therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water can be a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried slim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the B1,4GalT-V therapeutic, preferably in purified form, together with a suitable amount of carrier so as to provide the form for proper administration to the patient. The formulation should suit the mode of administration.

In a specific embodiment, the composition is formulated, in accordance with routine procedures, as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water or saline for injection can be provided so that the ingredients may be mixed prior to administration.

The B1,4GalT-V therapeutics of the invention can be formulated as neutral or salt forms. Pharmaceutically acceptable salts include those formed with free carboxyl groups such as those derived from hydrochloric, phosphoric, acetic, oxalic, tartaric acids, etc., those formed with free amine groups such as those derived from isopropylamine, triethylamine, 2-ethylamino ethanol, histidine, procaine, etc., and those derived from sodium, potassium, ammonium, calcium, and ferric hydroxides, etc.

Particular pharmaceutical compositions and dosage forms comprise a B1,4GalT-V therapeutic of the invention, or a pharmaceutically acceptable prodrug, salt, solvate, or clathrate thereof, optionally in combination with one or more additional active agents.

A. Routes of Administration

The pharmaceutical compositions of the present invention may be administered by any particular route of administration including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intraosseous, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, iontophoretic means, or transdermal means.

B. Dosage Determinations

In general, the pharmaceutical compositions disclosed herein may be used alone or in concert with other therapeutic agents at appropriate dosages defined by routine testing in order to obtain optimal efficacy while minimizing any potential toxicity. The dosage regimen utilizing a composition of the present invention may be selected in accordance with a variety of factors including type, species, age, weight, sex, medical condition of the patient; the severity of the condition to be treated; the route of administration; the renal and hepatic function of the patient; and the particular composition employed. A physician of ordinary skill can readily determine and prescribe the effective amount of the drug required to prevent, counter, or arrest the progress of the condition.

Optimal precision in achieving concentrations of drug within the range that yields maximum efficacy with minimal toxicity may require a regimen based on the kinetics of the composition's availability to one or more target sites. Distribution, equilibrium, and elimination of a drug may be considered when determining the optimal concentration for a treatment regimen. The dosages of a composition disclosed herein may be adjusted when combined to achieve desired effects. On the other hand, dosages of these various therapeutic agents may be independently optimized and combined to achieve a synergistic result wherein the pathology is reduced more than it would be if either agent were used alone.

In particular, toxicity and therapeutic efficacy of a composition disclosed herein may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effect is the therapeutic index and it may be expressed as the ratio $LD_{50}/ED_{50}$. Compositions exhibiting large therapeutic indices are preferred except when cytotoxicity of the composition is the activity or therapeutic outcome that is desired. Although compositions that exhibit toxic side effects may be used, a delivery system can target such compositions to the site of affected tissue in order to minimize potential damage to uninfected cells and, thereby, reduce side effects. Generally, the compositions of the present invention may be administered in a manner that maximizes efficacy and minimizes toxicity.

Data obtained from cell culture assays and animal studies may be used in formulating a range of dosages for use in humans. The dosages of such compositions lie preferably within a range of circulating concentrations that include the $ED_{50}$ with little or no toxicity. The dosage may vary within this range depending upon the dosage form employed and the route of administration utilized. For any composition used in the methods of the invention, the therapeutically effective dose may be estimated initially from cell culture assays. A dose may be formulated in animal models to achieve a circulating plasma concentration range that includes the $IC_{50}$ (the concentration of the test composition that achieves a half-maximal inhibition of symptoms) as determined in cell culture. Such information may be used to accurately determine useful doses in humans. Levels in plasma may be measured, for example, by high performance liquid chromatography.

Moreover, the dosage administration of the compositions of the present invention may be optimized using a pharmacokinetic/pharmacodynamic modeling system. For example, one or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile. See WO 00/67776, which is entirely expressly incorporated herein by reference.

C. Dosages

More specifically, the compositions may be administered in a single daily dose, or the total daily dosage may be administered in divided doses of two, three, or four times daily. In the case of oral administration, the daily dosage of the compositions may be varied over a wide range from about 0.1 ng to about 1,000 mg per patient, per day. The range may more particularly be from about 0.001 ng/kg to 10 mg/kg of body weight per day, about 0.1-100 μg, about 1.0-50 μg or about 1.0-20 mg per day for adults (at about 60 kg).

The daily dosage of the pharmaceutical compositions may be varied over a wide range from about 0.1 ng to about 1000 mg per adult human per day. For oral administration, the compositions may be provided in the form of tablets containing from about 0.1 ng to about 1000 mg of the composition or 0.1, 0.2, 0.5, 1.0, 2.0, 5.0, 10.0, 15.0, 100, 150, 200, 250, 300, 350, 400, 450, 500, 550, 600, 650, 700, 800, 900, or 1000 milligrams of the composition for the symptomatic adjustment of the dosage to the patient to be treated. An effective amount of the composition is ordinarily supplied at a dosage level of from about 0.1 ng/kg to about 20 mg/kg of body weight per day. In one embodiment, the range is from about 0.2 ng/kg to about 10 mg/kg of body weight per day. In another embodiment, the range is from about 0.5 ng/kg to about 10 mg/kg of body weight per day. The compositions may be administered on a regimen of about 1 to about 10 times per day.

In the case of injections, it is usually convenient to give by an intravenous route in an amount of about 0.0001 μg-30 mg, about 0.01 μg-20 mg or about 0.01-10 mg per day to adults (at about 60 kg). In the case of other animals, the dose calculated for 60 kg may be administered as well.

Doses of a composition of the present invention can optionally include 0.0001 μg to 1,000 mg/kg/administration, or 0.001 μg to 100.0 mg/kg/administration, from 0.01 μg to 10 mg/kg/administration, from 0.1 μg to 10 mg/kg/administration, including, but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 μg/ml serum concentration per single or multiple administration or any range, value or fraction thereof.

As a non-limiting example, treatment of humans or animals can be provided as a one-time or periodic dosage of a composition of the present invention 0.1 ng to 100 mg/kg such as 0.0001, 0.001, 0.01, 0.1 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Specifically, the compositions of the present invention may be administered at least once a week over the course of several weeks. In one embodiment, the pharmaceutical compositions are administered at least once a week over several weeks to several months. In another embodiment, the pharmaceutical compositions are administered once a week over four to eight weeks. In yet another embodiment, the pharmaceutical compositions are administered once a week over four weeks.

More specifically, the compositions may be administered at least once a day for about 2 days, at least once a day for about 3 days, at least once a day for about 4 days, at least once a day for about 5 days, at least once a day for about 6 days, at least once a day for about 7 days, at least once a day for about 8 days, at least once a day for about 9 days, at least once a day for about 10 days, at least once a day for about 11 days, at least once a day for about 12 days, at least once a day for about 13 days, at least once a day for about 14 days, at least once a day for about 15 days, at least once a day for about 16 days, at least once a day for about 17 days, at least once a day for about 18 days, at least once a day for about 19 days, at least once a day for about 20 days, at least once a day for about 21 days, at least once a day for about 22 days, at least once a day for about 23 days, at least once a day for about 24 days, at least once a day for about 25 days, at least once a day for about 26 days, at least once a day for about 27 days, at least once a day for about 28 days, at least once a day for about 29 days, at least once a day for about 30 days, or at least once a day for about 31 days.

Alternatively, the compositions may be administered about once every day, about once every 2 days, about once every 3 days, about once every 4 days, about once every 5 days, about once every 6 days, about once every 7 days, about once every 8 days, about once every 9 days, about once every 10 days, about once every 11 days, about once every 12 days, about once every 13 days, about once every 14 days, about once every 15 days, about once every 16 days, about once every 17 days, about once every 18 days, about once every 19 days, about once every 20 days, about once every 21 days, about once every 22 days, about once every 23 days, about once every 24 days, about once every 25 days, about once every 26 days, about once every 27 days, about once every 28 days, about once every 29 days, about once every 30 days, or about once every 31 days.

The compositions of the present invention may alternatively be administered about once every week, about once every 2 weeks, about once every 3 weeks, about once every 4 weeks, about once every 5 weeks, about once every 6 weeks, about once every 7 weeks, about once every 8 weeks, about once every 9 weeks, about once every 10 weeks, about once every 11 weeks, about once every 12 weeks, about once every 13 weeks, about once every 14 weeks, about once every 15 weeks, about once every 16 weeks, about once every 17 weeks, about once every 18 weeks, about once every 19 weeks, about once every 20 weeks.

Alternatively, the compositions of the present invention may be administered about once every month, about once every 2 months, about once every 3 months, about once every 4 months, about once every 5 months, about once every 6 months, about once every 7 months, about once every 8 months, about once every 9 months, about once every 10 months, about once every 11 months, or about once every 12 months.

Alternatively, the compositions may be administered at least once a week for about 2 weeks, at least once a week for about 3 weeks, at least once a week for about 4 weeks, at least once a week for about 5 weeks, at least once a week for about 6 weeks, at least once a week for about 7 weeks, at least once a week for about 8 weeks, at least once a week for about 9 weeks, at least once a week for about 10 weeks, at least once a week for about 11 weeks, at least once a week for about 12 weeks, at least once a week for about 13 weeks, at least once a week for about 14 weeks, at least once a week for about 15 weeks, at least once a week for about 16 weeks, at least once a week for about 17 weeks, at least once a week for about 18 weeks, at least once a week for about 19 weeks, or at least once a week for about 20 weeks.

Alternatively the compositions may be administered at least once a week for about 1 month, at least once a week for about 2 months, at least once a week for about 3 months, at least once a week for about 4 months, at least once a week for about 5 months, at least once a week for about 6 months, at least once a week for about 7 months, at least once a week for about 8 months, at least once a week for about 9 months, at least once a week for about 10 months, at least once a week for about 11 months, or at least once a week for about 12 months.

D. Combination Therapy

It would be readily apparent to one of ordinary skill in the art that the compositions of the present invention (e.g., siRNAs, antisense oligonucleotides, D-PDMP, and other agents described herein) can be combined with one or more of other anti-cancer therapies. The determination of the identity and amount of second anti-cancer agent(s) for use in a method of the present invention can be readily made by ordinarily skilled medical practitioners using standard techniques known in the art, and will vary depending on the type and severity of cancer being treated.

The compositions of the present invention and second anti-cancer agents can be administered simultaneously or sequentially by the same or different routes of administration. In particular, the compositions of the present invention can be administered simultaneously or sequentially with antineoplastic agents such as antimetabolites, alkylating agents, spindle poisons and/or intercalating agents, and proteins such as interferons.

Examples of particular second anti-cancer agents include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthracycline; anthramycin; aromatase inhibitors; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; chlorodeoxyadenosine; cirolemycin; cisplatin; cladribine; corticosteroids; crisnatol mesylate; cyclophosphamide; cytarabine; cytosine arabinose; dacarbazine; dactinomycin; daunorubicin hydrochloride; decitabine; deoxyconformycin; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflomithine hydrochloride; elsamnitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; folinic acid; fosquidone; fostriecin sodium; gemcitabine; gemcitabine hydrochloride; hydroxyurea; idarubicin hydrochloride; ifosfamide; ilmofosine; interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; leucovorin; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; myelopurine; navelbine; nitrosoureas camustine; nocodazole; nogalamycin; ormaplatin; oxaliplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; progestins; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; taxane; tecogalan sodium; tegafur; teloxantrone hydrochloride; temoporfin; teniposide; teroxirone; testolactone; thiamiprine; thioguanine; thiotepa; tiazofurin; tirapazamine; topoisomerase inhibitors; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Still other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; amino levulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard second anti-cancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonennin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urolinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

In another aspect, the B1,4GalT-V therapeutic agents may be combined with other agents including, but not limited to, immunomodulatory agents, anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steroids, non-steriodal anti-inflammatory drugs (e.g., aspirin, ibuprofen, diclofenac, and COX-2 inhibitors), and leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), anti-viral agents, and antibiotics (e.g., dactinomycin (formerly actinomycin), bleomycin, erythomycin, penicillin, mithramycin, and anthramycin (AMC)).

In various embodiments, the B1,4GalT-V therapeutic agent in combination with a second therapeutic agent may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In particular embodiments, two or more therapies are administered within the same patent visit.

In certain embodiments, one or more compounds of the present invention and one or more other therapies are cyclically administered. Cycling therapy involves the administration of a first therapy (e.g., a first B1,4GalT-V therapeutic agent) for a period of time, followed by the administration of a second therapy (e.g. a second B1,4GalT-V therapeutic agent, another anti-cancer agent, or another therapeutic agent) for a period of time, optionally, followed by the administration of a third therapy for a period of time and so forth, and repeating this sequential administration, e.g., the cycle in order to reduce the development of resistance to one of the therapies, to avoid or reduce the side effects of one of the therapies, and/or to improve the efficacy of the therapies. In certain embodiments, the administration of the combination therapy of the present invention may be repeated and the administrations may be separated by at least 1 day, 2 days, 3 days, 5 days, 10 days, 15 days, 30 days, 45 days, 2 months, 75 days, 3 months, or at least 6 months.

D. Kits

The present invention also provides kits for use in treating and/or diagnosing cancer. The kits of the present invention include one or more containers comprising B1,4GalT-V therapeutics (D-PDMP, siRNAs, antibodies, etc.), and in some embodiments, further comprise instructions for use in accordance with any of the methods described herein. The kit may further comprise a description of selecting an individual suitable or treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of the present invention are provided in suitable packaging. Suitable packaging include, but is not limited to, vials, bottles, jars, flexible packaging (e.g., sealed Mylar or plastic bags), and the like. Kits may optionally provide additional components such as buffers and interpretative information.

The instructions relating to the use of the therapeutic compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of the composition as disclosed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compositions and instructions for use and packaged in quantities sufficient for storage and use in pharmacies, for example, hospital pharmacies and compounding pharmacies.

EXAMPLES

Materials and Methods

Materials.

Human recombinant $VEGF_{165}$ and b-FGF was purchased from R&D Systems, Inc. (Minneapolis, Minn.). LacCer (from bovine milk and brain), glucosylceramide sphingosinel-phosphate and LacCer synthase inhibitor D-PDMP were obtained from Matreya, Inc. (Pleasant Gap, Pa.). Anti-human PECAM-1 mAb was purchased from R&D Systems, Inc. Secondary antibodies conjugated with horseradish peroxidase (HRP), Super Signal West Pico Chemiluminescence™ signal substrate solution and M-PER™ protein extraction kits were obtained from Pierce Biotechnology (Rockfield, Ill.). LY294002, $N^{\omega}$-nitro-L-arginine methyl ester (L-NAME) and 1-pyrrolodinecarbodithioicacid (PDTC) and suramin were obtained from Calbiochem (San Diego, Calif.). Dimethyl sphingosine was from Avanti Polar Lipids, Inc. (Alabaster, Ala.). Matrigel was purchased from BD Biosciences (Bedford, Mass.).

Collagenase A, elastase, and DNAse1 were purchased from Roche Diagnostics GmbH (Penzberg, Germany). BerEP4antibody against epithelial specific antigens, anti CD-45 (leukocyte common antigen) beads, anti CD14 beads and anti CD 64 beads were from Invitrogen Corporation (Carlsbad, Calif.). Antibodies against von Willebradt factor and mouse anti-human endothelial cell antibody (clone P1HiH12) were from Chemicon International (Temecula, Calif.).

Cell Culture.

Human umbilical vein endothelial cells (HUVEC), aortic endothelial cells (HAEC) and the endothelial cells growth media EGM™ were purchased from Lonza Walkersville, Inc. (Walkersville, Md.) and were cultured in EGM™ medium supplemented with 10% fetal bovine serum (FBS). Cells were grown in either 100 mm dishes or 6 well multi-dish chambers coated with 0.2% gelatin. Cells within passages 3 to 5 were used for the study. Prior to treatment, cells were maintained in serum-free EGM for 12 hrs and then stimulated with either agonists or antagonists. A human promonocytic cell line U-937 was obtained from ATCC (Manassas, Va.) and maintained in RPMI-1640 medium (Lonza Walkersville, Inc.) supplemented with 10% FBS.

Western Immunoblot Analysis.

Cells treated with agonists/antagonists were washed twice in PBS and lysed with mammalian protein extraction reagent (Pierce Biotechnology) supplemented with protease inhibitor cocktail (Roche Diagnostics GmbH). Protein content was determined using a Bradford dye binding assay kit from Bio-Rad Laboratories, Inc. (Richmond, Calif.) using BSA as standard. Twenty-five µg of cellular protein was resolved by 10% SDS-PAGE and then transferred to nitrocellulose membrane. After blocking (5% non-fat dry milk powder in Tris-buffered saline, pH 8.0 containing 0.05% Tween 20) for 1 hr at room temperature, membranes were incubated with appropriate primary antibodies. The membrane-bound primary antibodies were visualized by HRP-conjugated secondary antibody using a chemiluminescence kit. To verify equal loading, membranes were stripped and re-probed with β-actin antibody. The x-ray films were then densitometrically scanned using a Molecular Dynamics Image Scanner and analyzed using Image Quant software.

In Vitro Angiogenesis/Tube Formation Assay.

HUVECs were grown on 24-well culture plates and then exposed to various agonists/antagonists. After stipulated time points, cells were trypsinized, washed in sterile PBS twice and then reconstituted in EGM™ containing 2% FBS. In vitro angiogenesis assay was performed using a commercially available kit from Chemicon International. In brief, 50 µl of ECMatrix™ were placed on 96-well plates and allowed to polymerize at 37° C. for 2 hr. Then, HUVEC/HAEC ($5 \times 10^3$)

were suspended in 200 μl of EGM containing 2% FBS and pretreated with inhibitors±VEGF/bFGF/LacCer/S1P for an hr at 37° C., then the cells were added on top of the polymerized ECMatrix™ and incubated at 37° C. in 5% $CO_2$ atmosphere for 8-12 hrs. Tubes formed were documented using phase contrast microscope (NIKON) at 10× magnification. Images were acquired using CCD camera connected to computer with online image acquiring software AxioVision software (ZEISS). For quantification of tube lengths, images were exported to NIH Image J Software (http://rsb.info.hih.gov/ij/download.html). Results are shown as the mean tube length±SD (in um) for three photographic fields per experiment/well for at least three experiments per condition.

Transendothelial Migration (TEM) Assay.

TEM assays were performed as previously described. Wei et al., 320 BIOCHEM. BIOPHYS. RES. COMMUN. 1228-35 (2004). Briefly, HUVECs ($3\times10^5$/ml) were placed on 0.2% gelatin coated upper side of Costar® Transwell® inserts (12 mm diameter, 3.0 μm pore-size) (Corning Incorporated, Acton, Mass.) and allowed to reach confluence. Afterwards, the cells were incubated with 2% FBS plus growth factor free EGM for 6 hrs. Subsequently, $3\times10^6$/ml U-937 promonocytic cell line was added to the upper chamber of the insert and allowed to migrate for 10-12 hrs. At the end of incubation, the U-937 cells that migrated to the lower chamber were carefully aspirated and washed in PBS twice (1500 rpm, 10 min, 4° C.) and then counted using a Neubauer chamber.

In Vivo Assay of Angiogenesis in Nude Mice.

Female athymic nude mice were injected subcutaneously with 200 μA of Matrigel mixture, containing VEGF (4 μg/ml) and b-FGF (4 μg/ml). Two days later, D-PDMP (10 mg/kg) suspended in 5% Tween-80/0.85% NaCl and was injected intraperitoneally daily for ten days. Mice, injected with vehicle alone, served as control. Passaniti et al., 67 LAB. INVEST. 519-28 (1992). Next, Matrigel plugs were removed, fixed in 10% formalin/PBS, embedded in paraffin and sectioned. Sections were stained with trichrome-Masson stain and photographed. Tissues were also flash-frozen and the activity of LacCer synthase was measured.

LacCer Synthase Activity Assay.

The activity of LacCer synthase was measured using $^{14}$C-UDP-Gal as donor and GlcCer as substrate as described previously. See Chatterjee, S., 311 METHODS ENZYMOL. 73-81 (2000).

Isolation of Endothelial Cells from Human Colon Cancer, Normal Colon and SAGE Analysis of Various Isoforms of Human LacCer Synthases.

These studies were carried out in the laboratory of Dr. Kenneth Kinzler, Oncology Research Center at The Johns Hopkins University, School of Medicine, as follows. Institutional approval for the use of discarded human tissue material was obtained and all operations were conducted at 4° C. Strips of mucosa from the ascending colon from normal subjects and half of a tumor (golf ball size) were sliced and stored in 50 mL of DMEM. The crypts were removed and the samples were next bathed in 5 mM DTT for 20 min and 10 mM EDTA in PBS for 30 min. The latter procedure was repeated once. Then the samples were transferred to PBS and shaken for 1-2 min. The lamina propria and submucosa are minced into small pieces and digested with 2 mg/mL collagenase A, 250 ug/mL elastase, 25 μg/mlDNAse1 in DMEM+ by shaking for 2 hr at 37 C. Next, the tissue digests were filtered sequentially through 500 μm, 250 μm, 100 μm and 40 μm nylon filter mesh (Tetko, Inc., Elmsford, N.Y.). The cells were washed with PBS/BSA and centrifuged (1,200 rpm, 15 min at 4° C.). The clumps were removed by filtration using a 40 μm mesh filter. The pelleted cells were re-suspended in PBS/BSA solution and loaded onto a preformed 30% Percoll gradient and separated at 800×g for 15 min (4° C.). The top layer of cells which contains the majority of endothelial cells was harvested, washed with PBS/BSA and centrifuged (1200 rpm, 15 min). The cell pellets were re-suspended in PBS and transferred through a 25 μm nylon filter mesh. The filtrate was centrifuged for 7 min at 600 g at 4° C. The remaining enterocytes and tumor cells which can bind non-specifically to beads in the final magnetic separation were removed using M450 beads which were pre-bound to the BerEP4antibody against epithelial specific antigens. Likewise, most of the remaining leukocytes were removed using a cocktail of anti CD-45 (leukocyte common antigen), anti CD14 and anti CD 64 beads respectively. Following isolation, batches of endothelial cells were subject to immunostaining using antibodies against von Willebrandt factor located in Weibel-Palade bodies and mouse anti-human endothelial cell antibody (clone P1HiH12). Freshly isolated endothelial cells from normal colon and tumor tissue were subject to SAGE analysis using standardized protocols described by the Kinzler-Vogelstein laboratory previously. See Velculescu et al., 270 SCIENCE 484-87 (1995). The probes used to detect various mRNA transcripts of LacCer synthases e.g. B1,4 GalT-V, B1,4GalT-VIa and B1,4GalTVIb were synthesized at the Johns Hopkins University core facility and are presented in Table 1 (below).

Statistical Analysis.

All assays were performed in duplicates or triplicates and values were expressed as mean±S.E. Student's t-test was used to evaluate the statistical significance of data. $P<0.05$ were considered significant.

Example 1

B1,4-Galt-V is the Major LacCer Synthase in Human Tumor Endothelial Cells and is Significantly Upregulated Three isoforms of LacCer synthase have been described in the literature. These are: B1,4GalT-V, B1,4GalT-VIa and an alternatively spliced variant of B1,4GalT-VIa termed B1,4GalT-VIb. In collaboration with Dr. Kinzler of the Johns Hopkins Department of Oncology, the mRNA levels of three LacCer synthase iso forms in normal human endothelial cells were compared by Serial Analysis of Gene Expression (SAGE) with human colorectal cancer endothelial cells. A tag is a quantification of transcripts. It was approximately quantified that there are 6 and 27 transcripts/cell for normal and tumor endothelial cells, respectively.

No significant difference was found in the mRNA level for B1,4GalT-VIa and B1,4GalT-VIb in normal human endothelial vs. human tumor endothelial cells (present in insignificant amounts) in these two cell types. However, the most significant difference was with the mRNA level for B1,4GalT-V. This transcript was increased ~4.5 fold in human tumor endothelial cells as compared to normal human endothelial cells (Table 1). In contrast, B1,4GalT-II transcript was decreased and no change was seen with the other B1,4GalT transcripts including the B1,4GalT-VI. Collectively, such observations suggest that in human tumor endothelial cells, B1,4GalT-V is the predominant LacCer synthase whose transcript is significantly increased.

TABLE 1

The expression levels of mRNA for different isoforms of LacCer synthase in normal human colonic endothelial cells and human colonic tumor endothelial cells.

| LacCer synthase isoform | SAGE tag sequence | Tags (number of mRNA transcripts/cell) | |
|---|---|---|---|
| | | Normal endothelial cells | Tumor endothelial cells |
| B1, 4GalT-V | TCACAAAAGA (SEQ ID NO. 2) | 6 | 27 |
| B1, 4GalT-VIa | AGTGTCAGGG (SEQ ID NO. 3) | 0 | 0 |
| B1, 4GalT-VIb | TACCTCTGGT (SEQ ID NO. 4) | 0 | 0 |

Example 2

VEGF-Induced Tube Formation is Inhibited by Dimethyl-Sphingosine and Bypassed by LacCer but not Sphingosine-1-Phosphate Treatment of human umbilical vein endothelial cells (HU-VEC) with VEGF (10 ng/ml) lead to marked tube formation (FIG. 1B), as compared to control (FIG. 1A). VEGF-induced tube formation was abrogated by pre-treatment with dimethyl sphingosine (DMS) (FIG. 1C), a potent inhibitor of sphingosine kinase (SK). DMS also inhibited S1P-induced tube formation in HUVECs (FIG. 1D). Further, DMS inhibition of angiogenesis was by-passed by LacCer (FIG. 1E) but not by sphingosine-1-phosphate (S1P) (FIG. 1G). These observations suggest that LacCer could induce angiogenesis independent of S1P in endothelial cells.

Example 3

Figure 2:
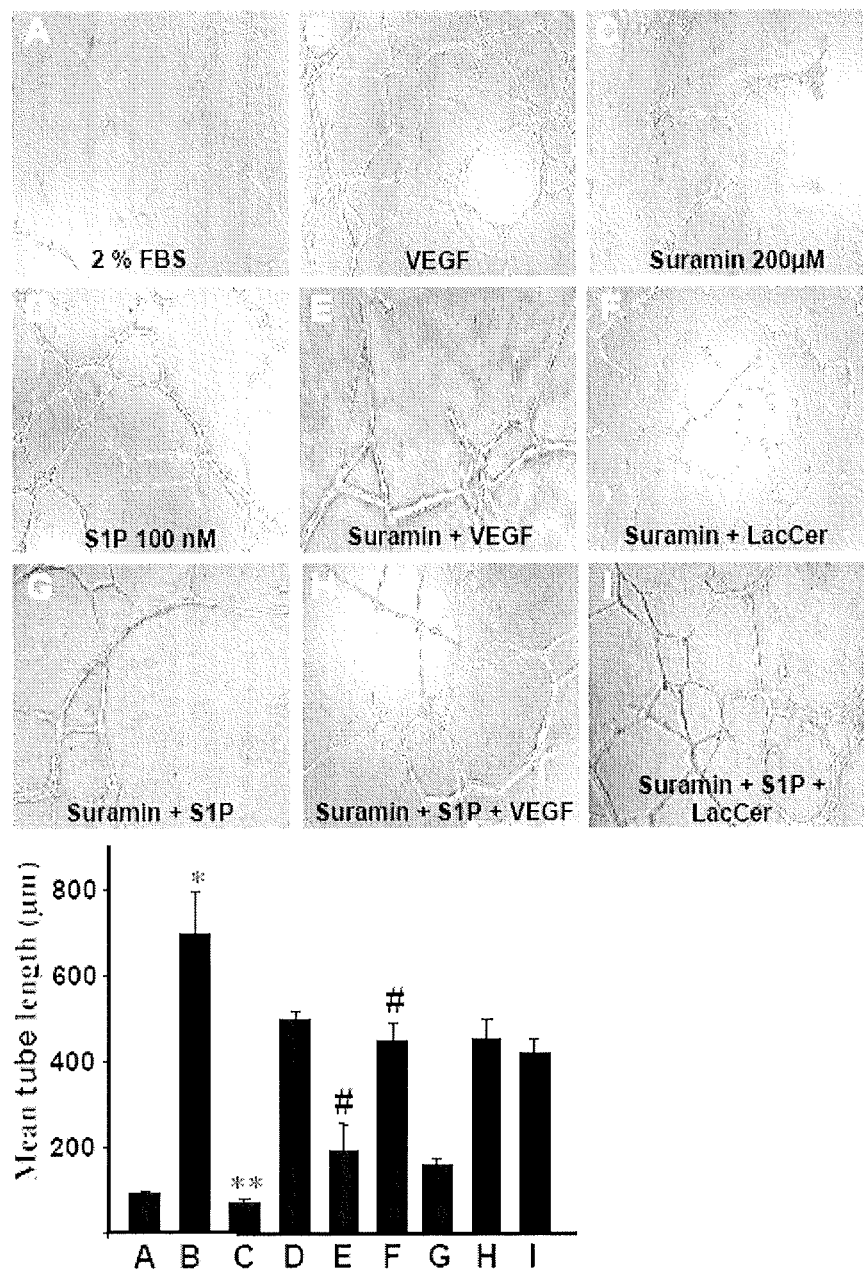
FIG. 2 shows that VEGF-induced tube formation was mitigated by surmain and this was bypassed by LacCer. *$P<0.001$ vs. 2% FBS; **$P<0.001$ vs. VEGF; +$P<0.001$ vs. VEGF; #$P<0.001$ vs. suramin+VEGF (n=9).

VEGF-Induced Tube Formation is Mitigated by Suramin and this was Bypassed by LacCer but not S1P Suramin is a specific inhibitor of G-protein coupled receptor (GPCR) activity and has been shown to inhibit VEGF- and S1P-induced angiogenesis in vitro. Chae et al., 114 J. CLIN. INVEST. 1082-89 (2004). Because S1P mediates its action via GPCR, this inhibitor was used to investigate whether LacCer could bypass the inhibitory effect of suramin on angiogenesis. It was found that suramin inhibited VEGF and S1P (FIG. 2 E,G), but not LacCer induced angiogenesis (FIG. 2F) in HUVECs. The inhibition of S1P-induced angiogenesis following treatment with suramin was by passed by LacCer (FIG. 2, I).

Example 4

Figure 3:
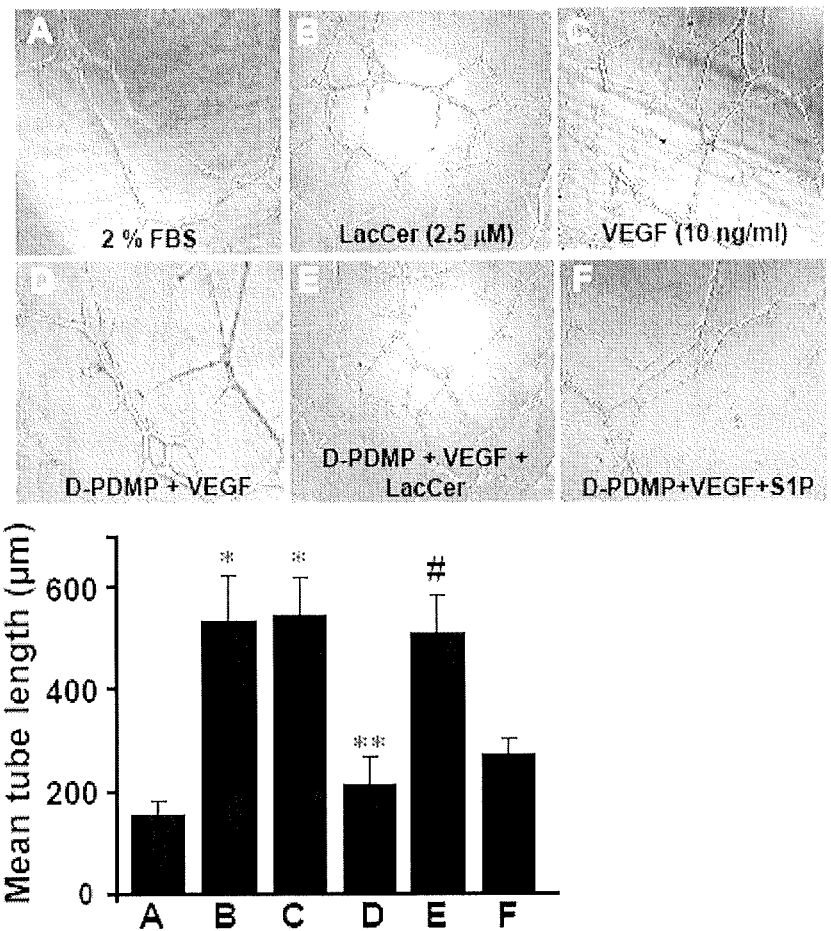
FIG. 3 established that VEGF-induced tube formation was inhibited by D-threo-1-phenyl-2-decanoyl-3-morpholino-1-propanol (D-PDMP) and this was bypassed by LacCer but not S1P. *$P<0.001$ vs. 2% FBS; **$P<0.001$ vs. VEGF; #$P<0.001$ vs. D-PDMP+VEGF (n=9).

VEGF-Induced Tube Formation is Mitigated by D-PDMP and this was Bypassed by LacCer but not S1P When HUVECs were treated with either VEGF or LacCer, they both induced tube formation (FIGS. 3B, 3C) and this was blunted by pretreatment with D-PDMP, a specific inhibitor of glucosylceramide synthase and LacCer synthase. After pre-treatment with D-PDMP, when the cells were co-incubated in the presence of VEGF and either LacCer/S1P, only LacCer but not S1P bypassed the inhibitory effect of VEGF-induced tube formation in the endothelial cells. Collectively, these results suggest that LacCer could induce angiogenesis independent of S1P receptor.

Example 5

Figure 4:
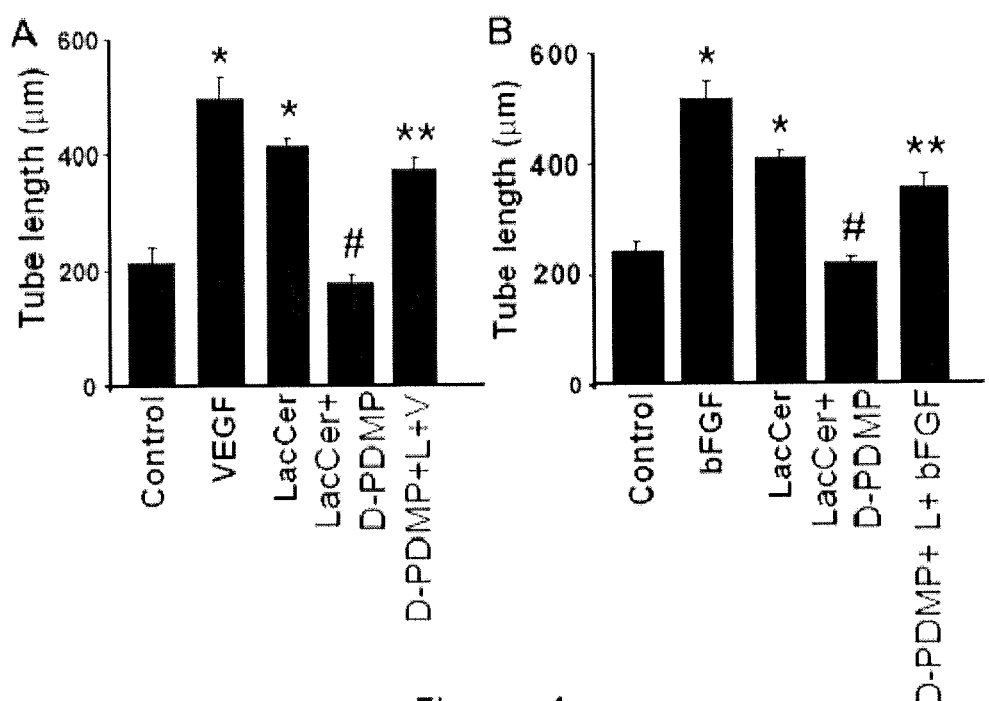
FIG. 4 shows that VEGF and bFGF induces tube formation in HAEC. (A) VEGF treatment of HAEC induced marked tube formation, which was inhibited by D-PDMP (20 µM) and this could be reversed by co-incubation of cells with LacCer (2.5 µM and VEGF). (B) bFGF treatment of HAEC induced marked tube formation, which was inhibited by D-PDMP (20 µM) and this could be reversed by co-incubation of cells with LacCer (2.5 µM and bFGF). *$P<0.001$ vs. control; #$P\ 0.01$ vs. VEGF/bFGF/LacCer; **$P<0.05$ vs. LacCer+D-PDMP (n=6).

VEGF and bFGF Induce and D-PDMP Inhibits Tube Formation in Human Arterial Endothelial Cells and this is Reversed by LacCer Next, D-PDMP was tested to determine whether it could inhibit VEGF/bFGF tube formation. As shown in FIG. 4A, the treatment of HAEC with VEGF markedly induced tube formation compared to control and this was inhibited by D-PDMP and could be reversed by pre-treatment with LacCer. Similar results were obtained in HAEC with basic fibroblast growth factor (bFGF) (FIG. 4B). Thus, both VEGF and bFGF recruit the LacCer synthase and LacCer pathway to induce tube formation in HAECs as well in HUVECs. See also Rajesh et al., 97 Circ. Res. 796-804 (2005).

Example 6

D-PDMP is not Cytotoxic and does not Induce Apoptosis in HUVEC

It was observed that VEGF stimulated proliferation in HUVEC, and D-PDMP (10-20 µM) reduced this effect significantly. However, D-PDMP alone did not alter cell proliferation and/or apoptosis in these cells. Apoptosis was estimated by DAPI staining for nuclear fragmentation and immunostaining for the release of cytochrome c from mitochondria. Because the basal medium in the assays contain 2% fetal bovine serum, it may exert a protective effect on these cells. Thus, D-PDMP does not impart toxic effects in HUVEC by way of decreasing basal cell proliferation or by inducing apoptosis (data not shown).

Example 7

D-PDMP Inhibits VEGF/bFGF-Induced Angiogenesis In Vivo in Mice

Figure 5:
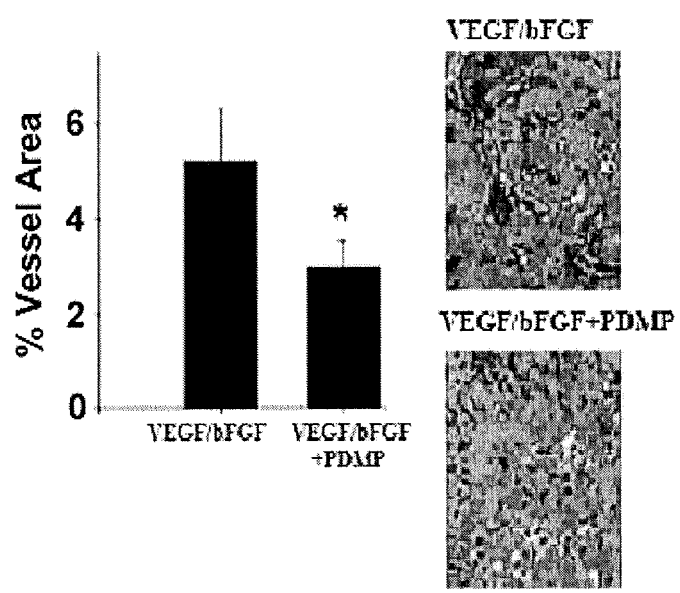
FIG. 5 demonstrates that VEGF/bFGF induce and PDMP mitigates in vivo angiogenesis in nude mice. In vivo angiogenesis was measured by Matrigel plug assay in nude mice. Matrigel mixed with VEGF and bFGF (4 µg/ml each) with or without D-PDMP was injected subcutaneously into the abdomen of nude mice. Plugs were retrieved after 10 days with daily dose of D-PDMP (10 mg/kg Intraperitoneal). Representative photos taken from Matrigel plugs shows blood vessels stained red and collagen blue. Approximately 10 fields were taken for each plug, and five plugs from each treated or control group were analyzed by Image Pro software. Results are expressed as percent micro vessel area means±SEM. *$P<0.001$ versus untreated controls (n=6).

As shown in FIG. 5, matrigel plug containing VEGF/bFGF (4 µg/ml) implantation in nude mice induced marked angiogenesis. Intraperitoneal (IP) administration of D-PDMP (10 mg/kg) for 10 days significantly inhibited angiogenesis in mice (n=6). The percentage of area occupied by blood vessels was measured by an imaging system (Image Pro). The corresponding bar graph shows that PDMP effect on mitigating VEGF/bFGF-induced angiogenesis was statistically significant (P<0.001). This was accompanied by a significant (39%) decrease in the activity of LacCer synthase (0.200±0.015 nmol/mg protein) in D-PDMP treated animals versus agonist treated mice (0.3139±0.015 nmol/h/mg protein). The results strongly suggest that indeed VEGF/bFGF can induce angiogenesis in mice and this can be mitigated by the inhibition of LacCer synthase activity with D-PDMP.

Example 8

Figure 6:
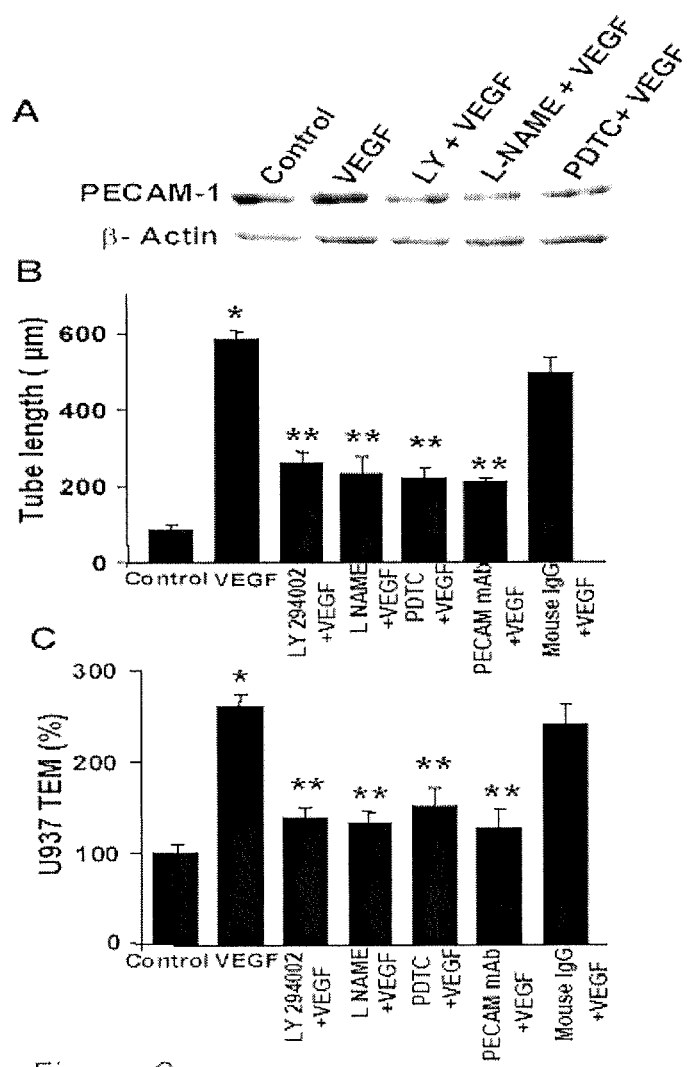
FIG. 6 shows that VEGF induced PECAM-1 expression, tube formation and monocyte TEM was abrogated by PI3K/eNOS/NF-κB pathway inhibitors. (A) Western blot analysis of PECAM-1 expression in HUVECs that were pretreated with either LY294002 (75 µM), L-NAME (100 µM) or PDTC (25 µM) for 90 min, followed by incubation with VEGF (25 ng/ml) for 4 hrs. (B) Depicts the quantification data for VEGF induced tube formation and inhibition by PI3K and NF-κB inhibitors. *$P<0.001$ vs. vehicle control; **$P<0.001$ vs. VEGF (n=6). (C) HUVECs were pretreated with either LY294002 (75 µM), L-NAME (100 µM), PDTC (25 µM), PECAM-1 monoclonal antibody (4 µg/ml) or mouse IgG (4 µg/ml) for 90 min, followed by incubation with VEGF (25 ng/ml) for 4 hrs and then U937 (monocyte) TEM assays were performed as described below. *$P<0.001$ vs. vehicle control; **$P<0.001$ vs. VEGF (n=6) (n=6).
Figure 7A:
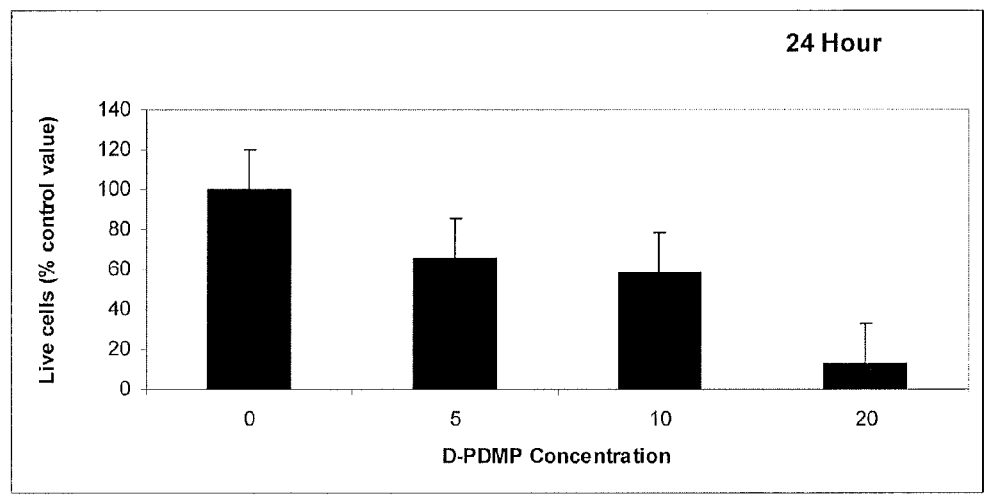
FIG. 7 shows the effect of increasing concentrations of D-PDMP on live cell counts at 24 hours (Panel A) and 96 hours (Panel B), as well as dead cell counts at 24 hours (Panel C) and 96 hours (Panel D) following treatment.
Figure 7B:
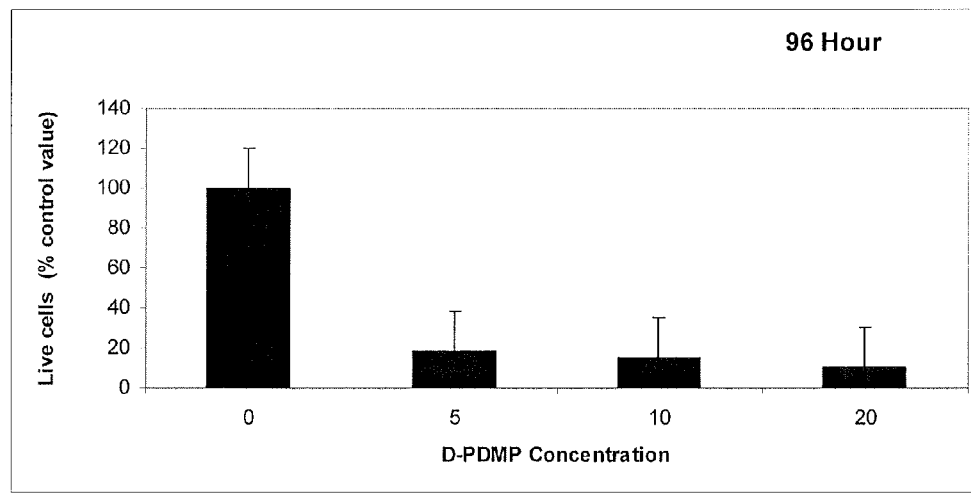
Figure 7C:
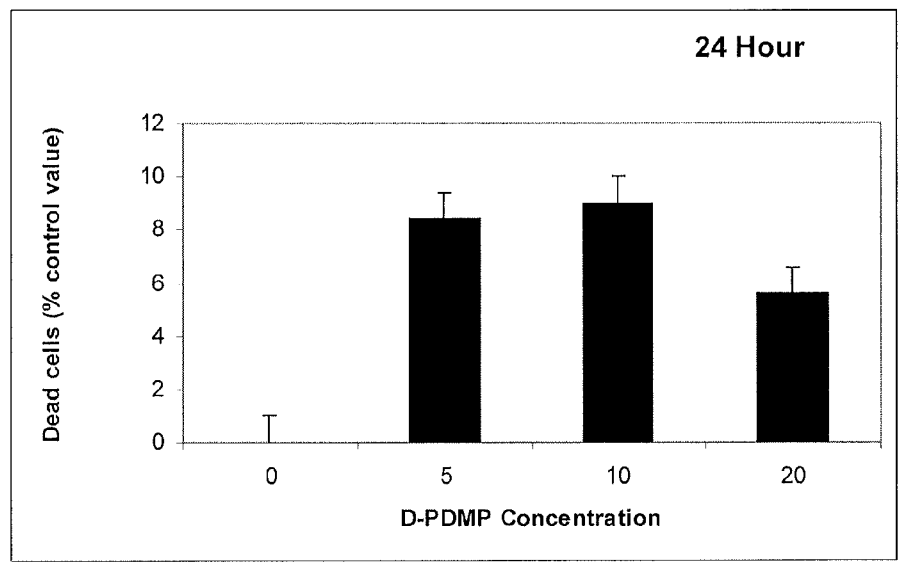
Figure 7D:
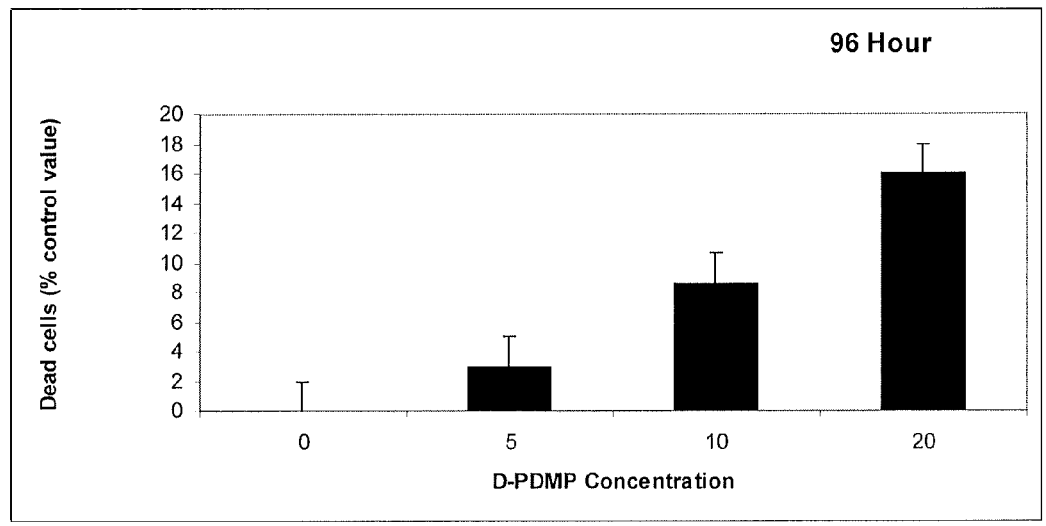
Figure 8:
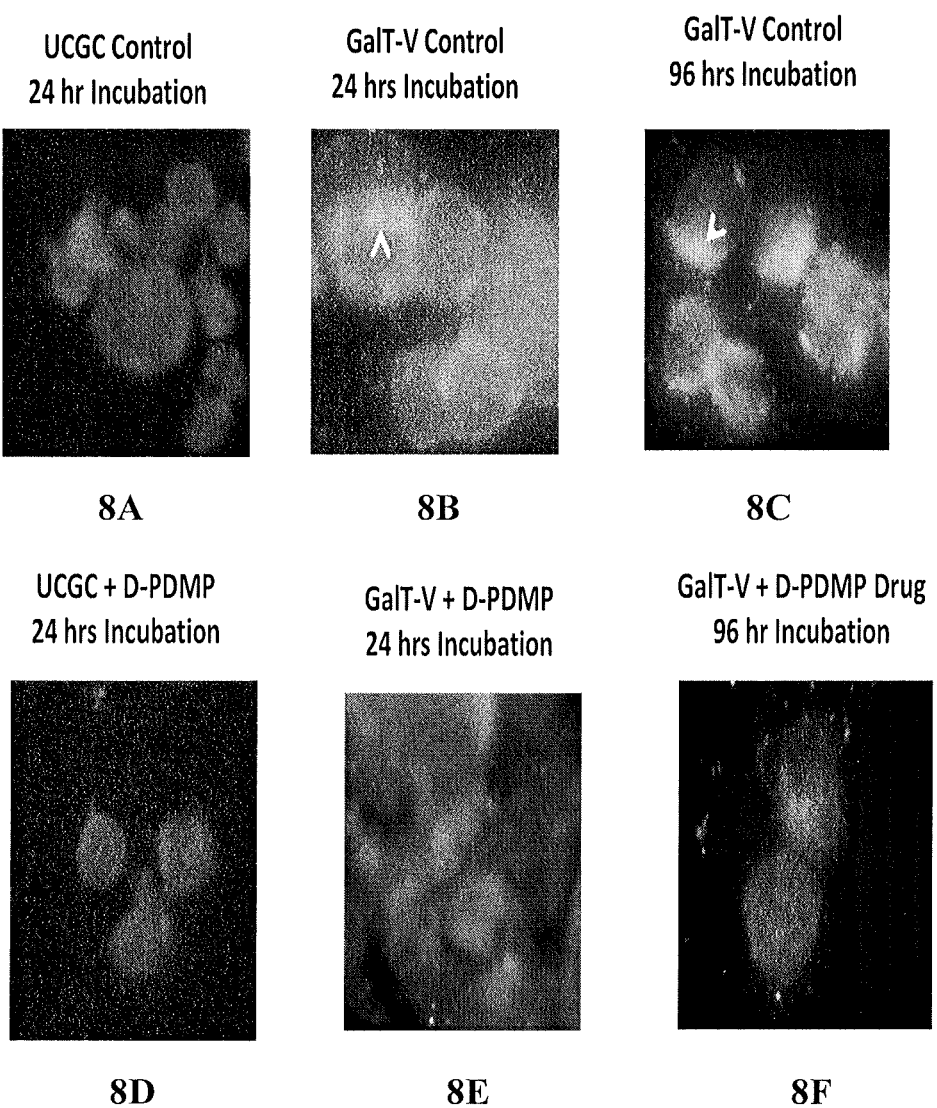
FIG. 8 depicts fluorescence images of cells following incubation periods with/without D-PDMP treatment on UCGC Control (Panel A, 24 hrs.), GalT-V Control (Panel B, 24 hours), GalT-V Control (Panel C, 96 hrs.), UCGC+D-PDMP (Panel D, 24 hrs.), GalT-V+D-PDMP (Panel E, 24 hrs.), and GalT-V+D-PDMP (Panel F, 96 hrs.).

Inhibition Of VEGF-Induced Phosphorylation Inhibits PECAM-1 Expression And Transendothelial Migration of Monocyte-Like Cells and Angiogenesis in HUVEC Previously it was observed that VEGF/LacCer-induced angiogenesis requires the expression of PECAM-1, an integral protein in human endothelial cells. Therefore, the upstream and downstream regulators of VEGF induced PECAM-1 expression was investigated. Treatment of HUVEC with VEGF induced marked expression of PECAM-1 (FIG. 6A), angiogenesis/tube formation (FIG. 6B) and in the transendothelial migration (TEM) of U-937 cells (FIG. 6C). However, pre-treatment of cells with LY294002, an inhibitor of PI3-kinase, reversed the stimulatory effect of VEGF on TEM as well as PECAM-1 protein expression and angiogenesis. Most importantly, VEGF-induced increase in angiogenesis in HUVEC was also markedly inhibited by the use of LY294002 (FIG. 6C). Further pre-treatment of HUVEC with 1-pyrrolodinecarbodithioicacid (PDTC), an inhibitor of NF-κB, also blunted VEGF-induced PECAM-1 expression, angiogenesis and monocyte TEM. These results indicate that PI3K and NF-κB are up-stream and down-stream intermediates that VEGF recruits to induce PECAM-1 expression, tube formation and monocyte TEM.

Example 9

A Simple, Sensitive And Specific Assay is Developed to Establish B1,4GalT-V as a Biomarker for Colon Cancer An ELISA-based assay is developed and used to determine the mass of B,14GalT-V in (a) spent medium in cultured human colorectal cancer cell line (HCR-116); (b) the blood of mice with colon cancer and (c) patients with colon cancer. B1,4GalT-V is localized predominantly in the Golgi apparatus in normal human cells, whereas it is also localized on the plasma membrane in cancer cells. Moreover, because cancer cells are known to shed the membranes, it is expected that B1,4GalT-V will also be shed in the spent medium in HCR-116 cells and/or in the blood in mice bearing tumors. Therefore, measurement of B1,4GalT-V level in the spent medium and blood samples can serve as a biomarker for colorectal cancer. Thus, by analogy to the PSA test for men with prostate cancer, the B1,4GalT-V assay may well serve as a novel biomarker of colorectal cancer and also serve as an indicator of the growth/metastasis of tumors and predict severity of the disease and/or efficacy of drug therapy.

First, a standardized ELISA protocol is employed to determine the level of B1,4GalT-V using pure B1,4GalT-V peptide and polyclonal rabbit IgG raised against this peptide (available in the inventor's laboratory). The sensitivity and specificity of the ELISA assay is determined by conducting competitive assays in the presence/absence of closely related enzyme/peptide such as B1,4GalT-VI and unrelated protein such as orosomucoid, a glycoprotein. Next, ELISA assays are conducted using the spent medium from cultured HCR-116 cells and compared with spent medium from cells from normal human colon. If the amount of enzyme shed in the spent medium is below the range of sensitivity of the ELISA assay, then the spent medium may have to be concentrated by microdialysis and filtration through a ~60 KDa molecular weight cut off filter disc. Having established the ELISA assay, the technology is then used to measure B1,4GalT-V level in blood samples from mice bearing colon cancer and subsequently in colorectal cancer patient samples. Blood samples are procured from the Johns Hopkins registry and/or NCI's registry of patients with various stages of colorectal cancer. If albumin and/or erythrocytes interfere with the assay, then these cells are removed by spinning down the blood samples. Next, albumin is removed using an affinity column coated with antibody against albumin. Each assay is conducted in sixtuplets and repeated on three separate occasions to establish the robustness of the assay. Also, the samples are blinded to assure confidentiality. Compliance with the institutional committee's guidelines for the use of samples from human subjects and applicable HIPPA rules is followed. Having achieved this milestone, FDA approval is sought to enter a multi-center double blind study to determine the validity of the assay in samples from colorectal cancer patients of multi-ethnic origin in the USA, Canada and Asia. A kit is developed for the assay of B1,4GalT-V as a biomarker for colon cancer and to determine the outcome of therapy. Statistical analysis is conducted using the student T test. A p-value of <0.05 is considered significant.

Example 10

Mitigation of Colorectal Cancer Using Inhibitors of B1,4 GalT-V

The growth and metastasis of a variety of cancers including colorectal cancer requires a constant supply of blood. Angiogenesis, the formation of new blood capillaries from existing ones, provides such blood supply to the tumor tissue and this is largely induced by vascular endothelial growth factor (VEGF). B-fibroblast growth factor (B-FGF) can also stimulate angiogenesis. As shown herein, VEGF/B-FGF-induced angiogenesis in human arterial endothelial cells can be mitigated by pharmacologicals such as D-PDMP and B1,4GalT-V siRNA. D-PDMP also mitigated VEGF/B-FGF-induced angiogenesis in immuno-compromised mice. And more recently, we have shown that D-PDMP can markedly reduce tumor volume and survival in a mice model of renal cancer. Hence, D-PDMP may well mitigate colorectal cancer in mice.

To determine the efficacy of D-PDMP in preventing growth and angiogenesis in human colorectal cancer cells, confluent culture of a human colon cancer cell line (HCR-116) is incubated with increasing concentrations of D-PDMP (1-50 uM) for 48 hrs. Cell proliferation and angiogenesis assays are conducted following protocols established in our laboratory. All cell based assays are conducted in sixtuplets. The spent medium and cell extracts are used to determine the shedding of B1,4GalT-V using ELISA assays. Fixed cells are used to determine reaction to antibody against B1,4GalT-V using immune-fluorescence microscopy.

To determine the efficacy of D-PDMP in preventing tumor growth and metastasis in human colon cancer cells and colorectal cancer in mice, tumor fragments from the human cancer cell line HCR-116 are surgically attached subcutaneously or to the serosal surface of the large intestine of immune deficient mice. See Nanda et al. 103 PROC. NATL. ACAD. SCI. USA 3351-65 (2006). Two days later, the experimental group of mice receive daily doses of D PDMP (5, 10, 20 mg/kg) by oral gavage. The control group of mice receive vehicle only. Three weeks later, the animals are euthanized by $CO_2$ asphyxia. The tumor tissue is subjected to in situ hybridization to determine tumor growth by determining VE cadherin $^+$ve blood cells. The number of vessels of various sizes is quantified in tumor tissue by formalin fixing and immunohistochemical staining with CD31 antigen (PECAM-1), a marker for vascular endothelium. VEGF, VEGFR2, B1,4GalT-V and LacCer immunostaining is conducted to assess their localization and quantitative distribution in the two groups of mice. Tumor tissue is also subjected to RT-PCR, western immunoblot assays and HPLC-mass spectrometry assays to determine the mass of B1,4GalT-V mRNA, protein and LacCer level, respectively. The blood samples are subjected to ELISA assay to determine whether drug treatment decreases the level of B1,4GalT-V and if there is a correlation with a decrease in tumor volume and metastasis. Mice (N=20) are used in each group of experiments.

To determine the efficacy of D-PDMP in interfering with the growth and metastasis in a mouse model of colon cancer, the protocol described above is utilized except that the tumor growth is allowed for 10 days following implantation of human colonic tumor tissue. Next, the optimal dose of D-PDMP is given daily by oral gavage for 3 weeks and tissues and blood samples are analyzed as above.

It is expected that D-PDMP will decrease the proliferation and angiogenesis of tumor cells in vitro and tumor growth and metastasis in vivo in a dose-dependent manner. Additional experiments on tumor growth prevention and metastasis are conducted and include combination therapy using D-PDMP, B1,4GalT-V peptides, siRNA for B1,4GalT-V, and other known anti-cancer drugs using the techniques and protocols described herein and known to those of ordinary skill in the art.

We claim:

1. A method for qualifying colorectal cancer status in a subject comprising: (a) measuring the B1,4GalT-V biomarker in a biological sample from said subject; (b) correlating the measurement with colorectal cancer status; and (c) treating the subject with a therapeutically effective amount of D-threo-1-phenyl-2-decanoyl-3-morpholino-1-propanol (D-PDMP) when the colorectal cancer status correlates with colorectal cancer.

2. The method of claim 1, wherein said B1,4GalT-V biomarker is measured by immunoassay.

3. The method of claim 1, wherein said biological sample is selected from the group consisting of blood, serum, plasma, stool, and tissue.

* * * * *